US009435798B2

(12) United States Patent
Eersels et al.

(10) Patent No.: US 9,435,798 B2
(45) Date of Patent: *Sep. 6, 2016

(54) HEAT-TRANSFER RESISTANCE BASED ANALYSIS OF BIOPARTICLES

(71) Applicants: IMEC, Leuven (BE); Universiteit Hasselt, Diepenbeek (BE)

(72) Inventors: Kasper Eersels, Leuven (BE); Marloes Peeters, Leuven (BE); Anitha Ethirajan, Leuven (BE); Bart Van Grinsven, Leuven (BE); Ward De Ceunick, Leuven (BE); Patrick Wagner, Leuven (BE)

(73) Assignees: IMEC, Leuven (BE); Universiteit Hasselt, Hasselt (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/192,931

(22) Filed: Feb. 28, 2014

(65) Prior Publication Data

US 2014/0242605 A1   Aug. 28, 2014

(30) Foreign Application Priority Data

Feb. 28, 2013  (EP) .................................. 13157264

(51) Int. Cl.
*G01N 33/543* (2006.01)
*G01N 25/18* (2006.01)

(52) U.S. Cl.
CPC ........ *G01N 33/54313* (2013.01); *G01N 25/18* (2013.01); *G01N 33/54373* (2013.01); *G01N 2600/00* (2013.01)

(58) Field of Classification Search
None
See application file for complete search history.

(56) References Cited

U.S. PATENT DOCUMENTS

| 5,992,505 A | 11/1999 | Moon | |
|---|---|---|---|
| 2003/0059807 A1 | 3/2003 | Roach | |
| 2004/0126814 A1* | 7/2004 | Singh et al. | 435/7.1 |
| 2006/0078999 A1* | 4/2006 | Bell et al. | 436/147 |

FOREIGN PATENT DOCUMENTS

| WO | 2004/079001 A1 | 9/2004 |
|---|---|---|
| WO | 2011023916 A1 | 3/2011 |
| WO | 2012/076349 A1 | 6/2012 |

OTHER PUBLICATIONS van Grinsven et al., Heat-Transfer Resistance at Solid-Liquid Interfaces: A Tool for the Detection of Single-Nucleotide Polymorphisms in DNA, vol. 6, No. 3, Published Feb. 22, 2012, pp. 2712-2721.*

(Continued)

*Primary Examiner* — Rebecca Martinez
(74) *Attorney, Agent, or Firm* — McDonnell Boehnen Hulbert & Berghoff LLP

(57) ABSTRACT

A bio-sensing device suitable for the detection and/or characterization of target bioparticles and corresponding method is described. The bio-sensing technique is based on the impact on the heat transfer resistivity value of bioparticles binding in binding cavities of a structured substrate. By sensing temperatures and determining a heat transfer resistivity value based thereon, a characteristic of the target bioparticles can be derived.

15 Claims, 15 Drawing Sheets

(56) References Cited

OTHER PUBLICATIONS

Hayden O et al: "Mass-sensitive detection of cells, viruses and enzymes with artificial receptors", Sensors and Actuators B: Chemical: International Journal Devoted to Research and Development of Physical and Chemical Transducers, Elsevier S.A, Switzerland, vol. 91, No. 1-3, Jun. 1, 2003, pp. 316-319.

K.A. Velizhanin et al., "Driving Denaturation: Nanoscale thermal transport as a probe of DNA melting," Physical Review, vol. 83, No. 5, May 1, 2011, pp. 1-7.

* cited by examiner

HEAT-TRANSFER RESISTANCE BASED ANALYSIS OF BIOPARTICLES

CROSS-REFERENCE TO RELATED APPLICATIONS

This application claims the benefit of priority of European Patent Application no. 13157264.6, filed Feb. 28, 2013, which is hereby incorporated by reference herein in its entirety.

FIELD OF THE INVENTION

The present disclosure is related to detection and/or characterisation of bioparticles. In particular, the present invention relates to a method and system for detecting and/or characterizing micrometer sized cells and small organic molecules.

BACKGROUND OF THE INVENTION

Molecularly imprinted polymers (MIPs) can be used for detecting chemical substances in complex mixtures. In modern day research these polymers are of increasing interest for bioanalytical applications. Advantages of using these MIPs include easy and cheap production, mechanical, chemical and thermal stability, reusability and unlimited shelf life. In recent years the concept of molecular imprinting has been extended to surface imprinting of thin polymer films with micrometer sized cells (to create so-called surface imprinted polymers or SIPs) for the detection of proteins, glycoproteins, plant viruses, human viruses, bacteria, pollen, yeast cells but also mammalian red blood cells. The detection of cells using biosensors described in literature is done by gravimetric detection, electronic read-out platforms or micro-fluidic techniques. However these techniques are often time-consuming, provide difficulties for analysis or they require expensive equipment.

A low-cost sensor platform that is able to differentiate between cells with slight differences in shape, size and functionalities in functional groups on their surface would be a valuable tool in modern day research.

WO2012076349A1 discloses a method and system for characterising bioparticles such as DNA and/or RNA duplexes. WO2012076349A1 discloses that it was surprisingly found that a higher heat-transfer resistance between a sensor surface covered with a single-stranded molecular DNA and/or RNA brush and the surrounding electrolyte exists compared to the low heat-transfer resistance of the double stranded DNA and/or RNA brush and the surrounding electrolyte below the melting transition. WO2012076349A1 describes that this physical phenomenon can be used for characterising and/or detecting DNA and/or RNA based molecules.

While WO2012076349A1 presents a valuable method and system to characterize and/or detect DNA and/or RNA based molecules, the system and method disclosed cannot be used for characterizing bioparticles such as cells or other molecules than DNA and/or RNA based molecules.

SUMMARY OF THE INVENTION

In certain aspects, the present invention provides methods and systems that allow characterisation of biological particles such as cells or molecules based on heat transfer resistance measurements.

It is an advantage of certain embodiments of the present invention that surprisingly an efficient characterisation of cells or molecules can be obtained, by using a particularly structured substrate.

One aspect of the present invention relates to a bio-sensing device suitable for the detection and/or characterization of target bioparticles, the bio-sensing device comprising a heating element for heating using a power, a sample holder comprising a structured substrate having a surface comprising a plurality of binding cavities in which target bioparticles can bind, the sample holder further being adapted for exposing the structured substrate at one side to the heating element, a first temperature sensing element for sensing a temperature at the side where the structured substrate can be exposed to the heating element and a second temperature sensing element for sensing a temperature at the side opposite thereto with respect to the structured substrate, a processing means programmed for calculating at least one heat transfer resistivity value based on temperature values obtained with the first temperature sensing element and the second temperature sensing element and the power for the heating element, for deriving a characteristic of the target bioparticles from said heat transfer resistivity value. It is an advantage of certain embodiments of the present invention that a system is provided that allows extending the technique of particle characterisation based on heat transfer resistivity to characterisation of bioparticles such as small organic molecules or living cells. It was surprisingly found that by providing a surface provided with binding cavities, characterisation of bioparticles such as small organic molecules or living cells can be achieved.

The structured substrate may be an imprinted substrate. It is an advantage of embodiments of the present invention that easy manufacturing techniques are available for the biosensing devices according to embodiments of the present invention.

The substrate may be a polymer. The surface of the binding cavities may be functionalised for specific binding of bioparticles to be detected or characterised. Advantageously, e.g. functional groups are provided that match functional groups at the bioparticles. Alternatively the functionalisation also may be done, for example, by complementary groups, organisms or fractions thereof, matching counterparts on the bioparticles.

In certain embodiments the bio-sensing device may be suitable for the detection and/or characterization of target bioparticles having an average diameter D and the binding cavities in the substrate may have an average diameter smaller in the range 1.5 times the average diameter D of the target bioparticles to 0.5 times the average diameter D of the target bioparticles.

For cell imprinted polymer layers, the average diameter of the imprints may correspond with between 0.5 and 0.9 times the average diameter of the cell. For small molecules (MIPs) the imprinting cavities advantageously may be bigger than the target molecule.

The binding cavities in the substrate may have an average diameter in the range 0.1 nm to 100 µm, e.g. depending on the application and particles envisaged. For SIP's the average diameter may be in the range 1 µm to 100 µm, e.g., between 2 µm and 25 µm, such as between 3 µm and 22 µm. For the small molecules (MIPs) the average diameter may be between 0.1 nm and 100 nm.

The structured substrate may be a surface imprinted substrate.

The structured substrate may be a molecularly imprinted substrate.

The processing means may be adapted for determining a heat transfer resistivity as function of temperature.

The biosensing device may comprise, at a side of the structured substrate opposite to the thermal element, a fluid compartment for exposing that side of the structured substrate to a fluid, the second temperature sensing element being positioned in the fluid compartment.

The processing means may be adapted for outputting, based on the at least one heat transfer resistivity, a characteristic of the target bioparticles.

The heating element may be controlled by a power resistor providing an input power.

The first temperature sensing element and/or the second temperature sensing element may be a thermocouple.

The biosensing device may comprise a controller for controlling the heating element and for controlling the temperature sensing elements for obtaining input power and temperature values for different temperatures as sensed with the first temperature sensing element. The present invention also relates to a method for characterising a target bioparticle, the method comprising obtaining a structured substrate having a surface comprising a plurality of binding cavities in which the target bioparticle can be bound, providing a heating power using a power at a first side of the structured substrate, sensing at least a temperature at the first side of the structured substrate and at a second side, opposite to the first side with respect to the structured substrate and calculating at least one heat transfer resistivity value based on the temperature values obtained at the first side and the second side and the power for deriving a characteristic of the target bioparticle from said heat transfer resistivity value.

The method may further comprise, prior to said providing a heating power and said sensing, rinsing the structured substrate with a fluid.

The method may comprise outputting a characteristic of the target bioparticle from said heat transfer resistivity value.

The calculating may comprise determining a heat transfer resistivity as function of temperature.

The method may comprise providing a sample fluid in contact with the surface comprising the plurality of binding cavities.

Said obtaining a structured substrate may comprise binding the target bioparticles to the surface comprising the plurality of binding cavities.

Another aspect of the present invention relates to a method for characterising a target bioparticle, the method comprising obtaining a structured substrate having a surface comprising a plurality of binding cavities in which the target bioparticle can be bound, contacting said structured substrate with said target bioparticles and an electrolytic solution having a neutral pH in a flow cell and measuring a first impedance value within said electrolytic solution, and then inducing a release of the target bioparticles from the binding cavities and then measuring a second impedance value within the flow cell after completion of the release of the bioparticles, and then obtaining a value representative for the impact of the release induction on the impedance of the electrolytic solution, and then deriving, based thereon, a characteristic of the target bioparticles.

In another aspect, the present invention relates to a bio-sensing device suitable for characterising a target bioparticle, the device comprising a flow cell equipped with an impedimetric analyzer, a structured substrate having a surface comprising a plurality of binding cavities in which the target bioparticle can be bound, exposed by at least the surface comprising the plurality of binding cavities of said substrate to the flow cell, a pumping system and switching valve connected to said flow cell, a first liquid supply comprising a electrolytic solution connected to said pumping system and switching valve, a release inducing means for releasing the bioparticles from the binding cavities, and a means for obtaining a value representative for the impact of release inducing means on the impedance of the electrolytic solution, and a means for deriving, based thereon, a characteristic of the target bioparticles. The release inducing means may be a second liquid supply for adding to said electrolytic solution a component inducing the release of the bioparticles from the binding cavities.

In another aspect, the present invention also relates to a controller for controlling a bio-sensing device suitable for characterising a bioparticle, the controller being programmed for providing control signals to the bio-sensing device for performing any of the methods described in embodiments of the present invention. Such a controller may be a computer program product.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 6a illustrates a time dependent response of T1 and T2. FIG. 6b illustrates the increasing of the heat-transfer resistance $R_{th}$ in function of time. Each arrow indicates an addition of cells corresponding to the arrows in FIG. 6a.

Figure 1:
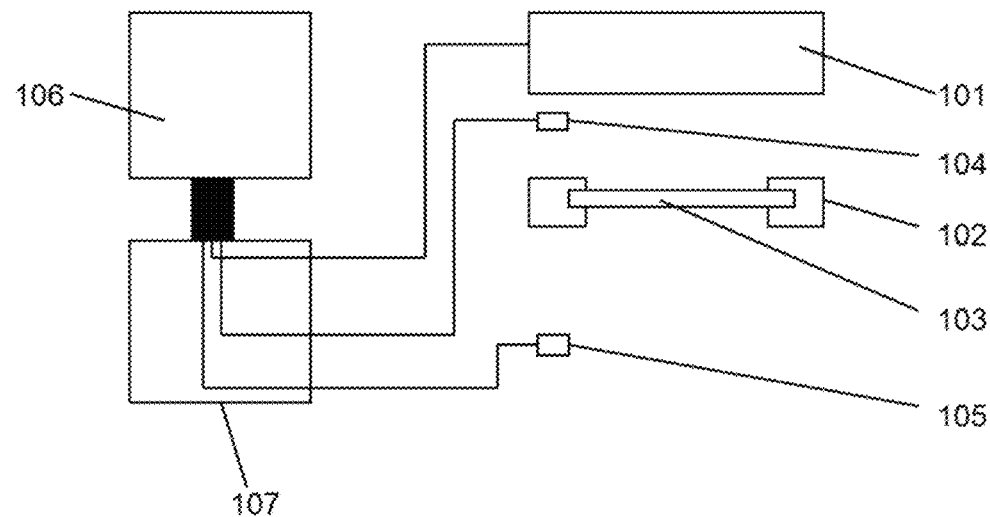
FIG. 1 illustrates a schematic view of a system according to one embodiment of the present invention.

Table 1 illustrates results of SIPs imprinted for NR8383 cells, RAW 264.7 and *Saccharomyces Cerevisiae*, illustrating features of certain embodiments of the present invention.

Table 2 illustrates results of SIPs imprinted for 2 different cancer cell types (MCF-7 and Jurkat), illustrating features of certain embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF THE INVENTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to a bioparticle this is defined as a relatively small or the smallest discrete portion or amount of biological material. This encompasses e.g. a cell or a molecule. Where reference is made to target bioparticles, reference is made to those particles targeted for characterising using the present technique.

Where in embodiments according to the present invention reference is made to heat transfer resistivity Rth, reference is made to the ratio of the temperature difference $\Delta T$ of the temperature at each side of the imprinted substrate comprising the target bioparticles to the input power P, i.e. Rth=ΔT/P.

Where in embodiments of the present invention reference is made to cavity or binding cavity, reference is made to an hollow space or hole in a substrate wherein the target bioparticles can position themselves.

Where in embodiments of the present invention reference is made to a structured substrate, reference is made to a substrate that does not have a flat surface, but that has shallow or deep cavities in the surface.

During experiments it was observed that detection of bioparticles other than DNA and/or RNA based molecules cannot be performed using the device and method as described in WO2012076349A1. This can e.g. be observed in FIG. 5b. The heat transfer resistivity Rth of a non-imprinted polymer in FIG. 5b doesn't show any substantial rise. This is in contrast with FIG. 5a which illustrates the heat transfer resistivity Rth of an imprinted polymer illustrating features of embodiments of the present invention. It was surprisingly found that bioparticles can be detected based on the heat-transfer resistance using structured substrates and that this can be used for characterising bioparticles.

In a first aspect of the invention, a bio-sensing device is disclosed for characterising and/or detection of target bioparticles. By way of illustration, embodiments of the present invention not limited thereto, a schematic overview of standard and optional components is shown in FIG. 1.

According to one embodiment of the present invention, the bio-sensing device 100 comprises a heating element 101. Such a heating element 101 may in one example be a block of solid material and a heating element, e.g. a power resistor providing an input power. In principle any type of heating element may be used. The heating element according to embodiments typically is adapted—e.g. in relative position with respect to the sample or sample-substrate—so that a temperature gradient is created over the sample or sample-substrate. Heating elements thus may be used that provide a heating source at one side of the sample or sample-substrate, which transfers through the sample, and then goes into the fluid positioned at the opposite side of the sample or sample-substrate (i.e. opposite to the heating element, with reference to the substrate.

The biosensor 100 furthermore comprises a sample holder 102. The sample holder 102 according to embodiments of the present invention comprises a structured substrate 103 having a surface comprising a plurality of binding cavities in which target bioparticles can bind. Such a structured substrate may for example be an imprinted substrate, although embodiments of the present invention are not limited thereto and e.g. a structured substrate based on laser ablation of cavities also can be used. The sample holder 102 furthermore is adapted for exposing the structured substrate at one side to the heating element.

The device 100 furthermore comprises a first temperature sensing element 104 for sensing a temperature at the side where the structured substrate 103 can be exposed to the heating element 101 and a second temperature sensing element 105 for sensing a temperature at the side opposite thereto with respect to the structured substrate 103. Such temperature sensing elements 104, 105 can be any type of temperature sensing elements 104, 105, one example being a thermocouple. The device 100 also may comprise more than two sensing elements, such as for example an array of temperature sensing elements, although for operating embodiments of the invention, two temperature sensing elements are sufficient.

Figure 2:
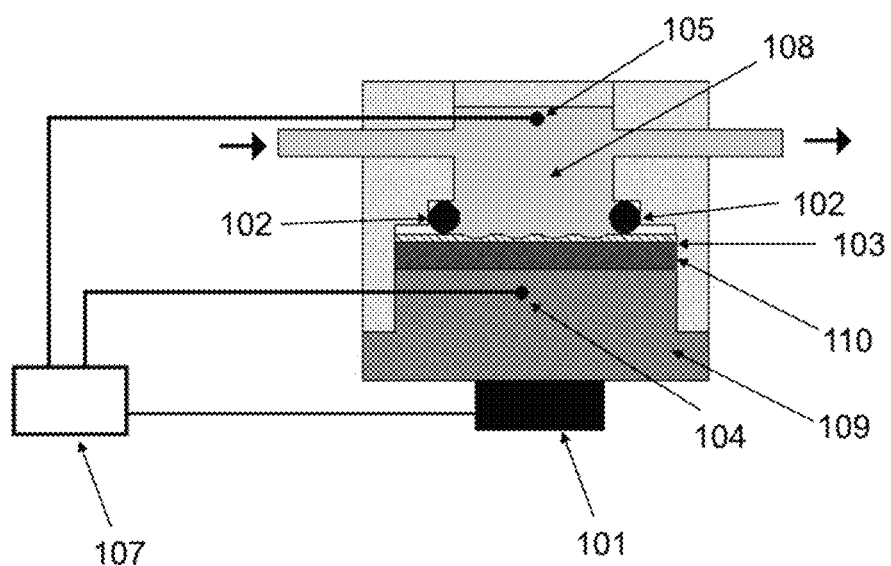
FIG. 2 illustrates a more detailed schematic view of an exemplary setup for measuring a change in heat-transfer capacity according to one embodiment of the present invention.

According to one embodiment of the invention, as illustrated in FIG. 2, the heating element 101 is in direct contact with a metal block 109 which is in direct contact with a metal carrier 110. Heat produced by the heating element 101 is transferred to the structured substrate 103 through the metal block 109 and the metal carrier 110. In a particular embodiment of the invention, the metal block 109 is a copper block. In a particular embodiment of the invention, the metal carrier 109 is an aluminium block.

According to one embodiment of the invention, the structured substrate 103 is a substrate layer deposited on the metal carrier 110. In a particular embodiment of the invention, the structured substrate 103 is a thin layer of polymer material, e.g. a thin layer of polyurethane. The thickness of such a layer may for example be one or a few micrometer. In one embodiment, this may be for example about 1.2 μm.

According to some embodiments of the present invention, the structured substrate 103 may be an imprinted substrate 103. Such an imprinted substrate may be a surface imprinted polymer (SIP). The device may then be especially suitable for detecting and/or characterising biological cells, although embodiments are not limited thereto. Advantageously, the biosensing device 100 may be used to differentiate between biological cells by slight differences in shape, size and functionalities in functional groups on their surface.

The structured surface may have cavities with a diameter between 0.5 times and 1.5 times the average diameter of the particles envisaged for detection with the sensing device. For cell imprinted polymer layers, the average diameter of the imprints may correspond with between 0.5 and 0.9 times the average diameter of the cell. For small molecules (MIPs) the imprinting cavities advantageously may be bigger than the target molecule.

The binding cavities in the substrate may have an average diameter in the range 0.1 nm to 100 μm, e.g. depending on the application and particles envisaged. For SIP's the average diameter may be in the range 1 μm to 100 μm, e.g. between 2 μm and 25 μm, such as between 3 μm and 22 μm. For the small molecules (MIPs) the average diameter may be between 0.1 nm and 100 nm.

According to some embodiments of the present invention, the structured substrate 103 is a molecularly imprinted polymer (MIP). When using a surface imprinted polymer, the biosensing device 100 may be especially suitable for detecting molecules, although embodiments of the present invention are not limited thereto. Advantageously the biosensing device is able to perform fast and low-cost measurements in biological samples.

As indicated above, also other types of structured substrates 103 can be used, such as substrates structured using other types of imprinting, using laser ablation, by microspotting, by growing MIPs directly on the surface, by ion beam lithography, by ink-jetting, . . . Advantageously in some embodiments the cavities furthermore are functionalised, so that the inner surface of the cavities is designed to attract and/or specifically bind bioparticles. The functionalisation may be performed using e.g. functional groups, complementary groups, organisms or fractions thereof, . . . .

The biosensing device 100 furthermore comprises a processing means 106 programmed for calculating at least one heat transfer resistivity value based on temperature values obtained with the first temperature sensing element 104 and the second temperature sensing element 105 and an input power for the heating element 101.

According to embodiments of the present invention, the processing means 106 is programmed for using the calculated values for deriving a characteristic of the target bioparticles from said heat transfer resistivity value. In certain advantageous embodiments, the processor or processing means 106 is adapted for determining a heat transfer resistivity as function of temperature. The processing means 106 furthermore may be adapted for filtering the data, to improve signal to noise ratio. The processing means 106 furthermore may be adapted for deriving from the heat transfer resistivity values a characteristic of the target bioparticles. The processing means 106 may be adapted for taking into account experimental conditions, such as for example taking into account a heating rate or taking into account a position bioparticles with respect to the heating element (i.e. the bioparticles being at the side of the heating element with respect to the remaining part of the biocompatible substrate or at the opposite side thereof). The processing means 106 may be programmed for performing the above in an automated way. Such processing means 106 may be a software based processor, as well as a hardware based processor. It may for example make use of a predetermined algorithm, a look up table or a neural network for performing the processing.

According to some embodiments of the present invention, the biosensing device 100 may comprise a fluid compartment 108 for exposing the surface of the structured substrate 103 side comprising binding cavities to a fluid. The second temperature sensing element 105 being positioned in the fluid compartment 108. The fluid may be used for introducing the target bioparticles. The biosensing device 100 may comprise a flow cell comprising the fluid compartment 108 and furthermore comprising a pumping and/or valve system for transferring fluid from and to the fluid compartment 108. According to some particular embodiments, the flow cell may comprise a syringe system coupled to a Perspex flow cell with a suitable inner volume. The dimensions of said inner volume are optimised towards the final device goals. To set up a test device an example was shown having a suitable inner volume of around 110 µl. The effective area of the structured substrate surface depends on the dimensions of the flow cell and may be in one particular example of the order of around 28 mm2 exposed to the liquid. In some embodiments, the electrode may be sealed with an O-ring. The operation of the biosensing device may be controlled by a controller 107. A controller 107 may control the heat element and the temperature sensing elements for obtaining input power and temperature values. Such values may be obtained for different input powers, or—corresponding therewith—for different temperatures as sensed with the first temperature sensing element.

The system also may be equipped with electrodes for measuring an impedance or with a transparent bottom for measuring a fluorescence signal, as the measurement principle can be easily combined with other measurement techniques, e.g. for cross-checking. Further optional features and advantages may be as described in the example below.

In a second aspect, the present invention relates to a method for characterising and or detecting a target bioparticle. According to certain embodiments of the present invention, the method comprises obtaining a structured substrate having a surface comprising a plurality of binding cavities in which target bioparticles can be bound and providing a heating power using a power at a first side of the structured substrate. The latter results in a temperature gradient being present over the structured substrate and thus—when bound in the binding cavities—over the target bioparticles to be characterised and/or detected. The method also comprises sensing at least a temperature at the first side of the biocompatible substrate and at a second side, opposite to the first side with respect to the structured substrate. From these measurements and the power for the heating element used, according to certain embodiments of the present invention, at least one heat transfer resistivity value is calculated for detecting a target bioparticle or deriving a characteristic of the target bioparticle from the heat transfer resistivity value. By way of example, a savitskygolay filter could be used, although embodiments of the present invention are not limited thereto. In some embodiments, calculating at least one heat transfer resistivity value comprises determining the heat transfer resistivity as function of temperature, i.e. determining different heat transfer resistivity values at different temperatures. The calculating may furthermore include applying a filter for improving the signal to noise ratio. The temperature used as reference can in principle be chosen and may for example be the temperature sensed with the first temperature sensing element.

According to at least some embodiments of the invention, before providing a heating power, the structured substrate 103 is rinsed with a fluid. The forces exerted by the liquid flow are sufficient to break non-specific sticking between target bioparticle and binding cavities, which match only in size while missing chemical complementarities, therefore being less or not accurately bound. Bioparticles other than target bioparticles, which are only weakly and non-specifically bound are released from the structured substrate by rinsing while the target bioparticles remain sticking in the binding cavities of the structured substrate. As an advantage, the step of rinsing before providing a heating power enhances the selectivity of the target bioparticle detection. According to some embodiments of the invention, PBS can be used as rinsing fluid.

In certain embodiments according to the present invention, the structured substrate, more particularly a surface comprising a plurality of binding cavities in which a target bioparticles can bind is brought into contact with a fluid, and temperature sensing on this side occurs in the fluid. Obtaining the structured substrate can be performed in a plurality of manners. The structured substrate may be previously made. In some embodiments obtaining the imprinted substrate comprises inserting or positioning or fixing the structured substrate on or in the sample holder. The latter may correspond with inserting of a sample imprinted substrate (as a cartridge) into a cartridge reader.

In an embodiment of the invention, the structured substrate 103 is a surface imprinted substrate such as a surface imprinted polymer. In a first step, the surface imprinted polymer may be fabricated by polymerizing a Polyurethane mixture up to the gelling point. The Polyurethane gel is then diluted and spincoated on a transducer (e.g. a metal substrate). In a second step, template cells are spincoated on a PDMS stamp. In a third step, the PDMS stamp is pressed into the polyurethane layer. In a fourth step, the template cells and the stamp are removed, the layer can now specifically rebind a target cell.

In one embodiment of the invention, the structured substrate 103 is a molecularly imprinted substrate such as a molecularly imprinted polymer. In a first step a polymerizing template with functional monomers in a cross-linked matrix, in a second step the template is extracted. In a third step, binding cavities (nanocavities) are obtained which can specifically rebind a target molecule.

According to particular embodiments of the invention, a solution is provided over the structured substrate 103 for breaking down the membrane of the bioparticles which are bound to the surface of the imprinted substrate comprising binding cavities.

Further optional steps of the method according to embodiments of the present invention may be express the functionality of components described in the first aspect, or may correspond with features as described in the example below. Advantageously, the method may be used with a device according to an embodiment as described in the first aspect, although embodiments of the present invention are not limited thereto.

In a third aspect, the present invention also relates to a controller 107 adapted for controlling a heating element 101, temperature sensing elements 104, 105 and a processor 106 for performing a method according to various embodiments of the second aspect of the present invention. Such a controller 107 may be part of a system as described in the first aspect or may be suitable for communicating therewith. The controller 107 may be implemented as software—to be implemented on a processor—or may be implemented as hardware. The controller 107 may be implemented, such that after activation and obtaining the imprinted substrate, the sensing, calculating and where included the deriving step occurs in an automated and/or automatic way. The controller 107 may be programmed, e.g. it may include a microprocessor or an FPGA whereon a set of instructions are implemented. Alternatively, the controller 107 can be software based and thus may correspond with a computer program product. The present invention also relates to a computer program product providing, when run on a computer, the functionality of any of the methods as described in the second aspect. Such a computer program product may be carried on a data carrier, the invention thus also relating to a data carrier, such as a CD-ROM, a disk, a USB memory device, a DVD, a pc, a work station, . . . storing the computer program product in a machine readable form or to the transmission of such a computer program product over a network, e.g. local or wide area network.

By way of illustration, embodiments of the present invention not being limited thereto, examples are provided of a particular biosensor and of experimental results obtained therewith, illustrating features and advantages of embodiments according to the present invention.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired detection or characterisation properties sought to be obtained in embodiments of the present invention. At the very least, and not as an attempt to limit the application of the doctrine of equivalents to the scope of the claims, each numerical parameter should be construed in light of the number of significant digits and ordinary rounding approaches.

Example 1

Surface Imprinted Polymers

In a first particular example, the results are discussed for a device based on a structured substrate being a surface imprinted polymer substrate.

General Concept of the Device for Specific Cell Detection and Identification

The general principle of the heat-transfer device is shown in FIG. 2. The central element of the platform consist in the present example of an adjustable heating element that transfers the heat current via a copper block through an aluminum substrate (~1 by 1 cm2) covered with a thin (~1.2 μm) layer of polyurethane. This layer 103 is imprinted with templating cells. To ensure specificity, as a cross-reference, a complementary non imprinted polymer (NIP) is analyzed for each target.

Figure 3:
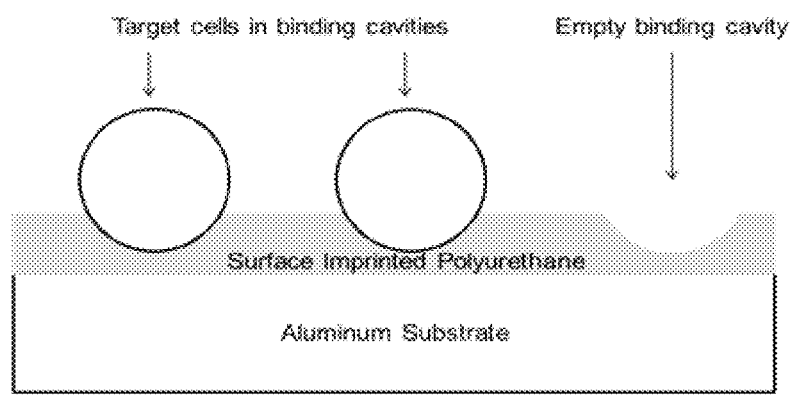
FIG. 3 and FIG. 4 illustrate the concept of the cells binding inside the binding cavities present on the surface of an imprinted substrate, as can be used according to certain embodiments of the present invention.

Surface imprinted polymers (SIPs) are able to rebind their templating cells (denoted as target cells during measurement descriptions) in a specific manner due to non-covalent interactions between functional groups on the surface of the target cells and functional groups distributed at complementary locations inside the binding cavities of the SIPs. The concept of rebinding is illustrated in FIG. 3a. The perfect fitting and binding of the target cells into the binding cavities of the SIP will cause a 'heat-transfer block', causing an increase in thermal resistance. This concept is illustrated in FIG. 3b.

The substrates were mechanically pressed with their backside on a copper block, serving as a heat provider. A thermocouple measured the internal temperature of the copper block T1 and this information was transferred to a PID controller responsible for keeping T1 constant at 37° C. Conductive silver paste was used to ensure a minimal heat-transfer loss between the copper and the aluminum substrate. The substrates were mounted horizontally in a Perspex home-made flow cell connected to a tubing system to enable addition of buffers and washing solutions over the samples. Sealing provided by an O-ring ensured a contact area of 28 mm2 between the sample and the liquid inside the flow cell. Minimal heat losses were observed along the seal, the heat was mainly transferred from the substrate to the liquid. The temperature of the liquid inside the flow cell T2 was measure by a second thermocouple, positioned exactly 1.7 mm above the solid-liquid interface. The heat-transfer measurements were performed in a temperature-stable environment Characterization of Polyurethane Layers Imprinted for NR8383 Cells To achieve a proof-of-principle, SIPs were created for 3 different targets. The rat alveolar macrophage cell line: NR8383 was used as a model templating cell. The mouse leukaemic monocyte macrophage cell line RAW 264.7 was used as an analogous cell type to assess selectivity. Yeast cells (*Saccharomyces cerevisiae*) were used as a second analogue cell type, these cell differ in origin and size from the macrophage cell lines. These cells are standard cell types used for the creation of SIPs.

Binding cavities in a typical polyurethane layer, were imprinted for e.g. using NR8383 have diameters ranging from 15-25 μm. The imprints were typically smaller than the native cells, as only part of the target cell is imprinted in the layer. Dektak measurements indicated that the layer thickness of a typical SIP is about 1.2 μm. A single imprint was characterized using an atomic force microscope. It was shown that the pit has a depth of approximately 1 μm.

Heat-Transfer Measurements

The SIP covered substrates were horizontally mounted in the flow-cell, liquids and cells were added to the flow-cell by the tubing system. Before each addition run, the system was stabilized in phosphate buffered saline (PBS) at a pH of 7.4. The PID controller ensured T1 remained constant during the measurements, cells were added to the flow-cell when T2 reached a stable level. After each addition of target cells to the flow cell the system was stabilized again and the cell was flushed with 0.1% sodium dodecyl sulphate solution (SDS) in order to break down the membrane of the cells bound to the layer. After stabilization of the signal, the flow cell was once more rinsed with PBS in order to remove the cells from the binding cavities.

Figure 4:
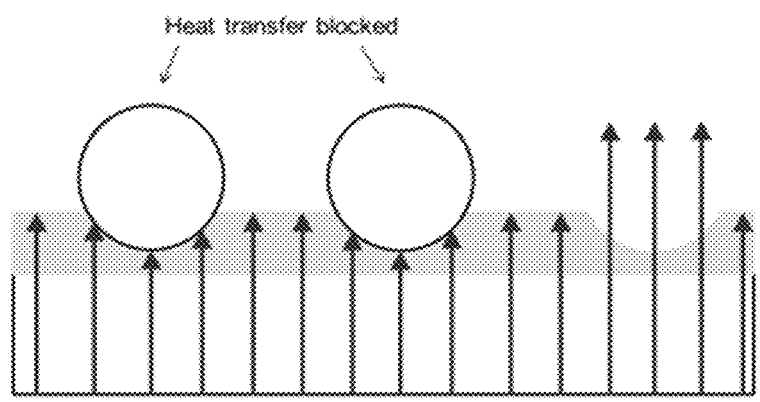
Figure 4A:
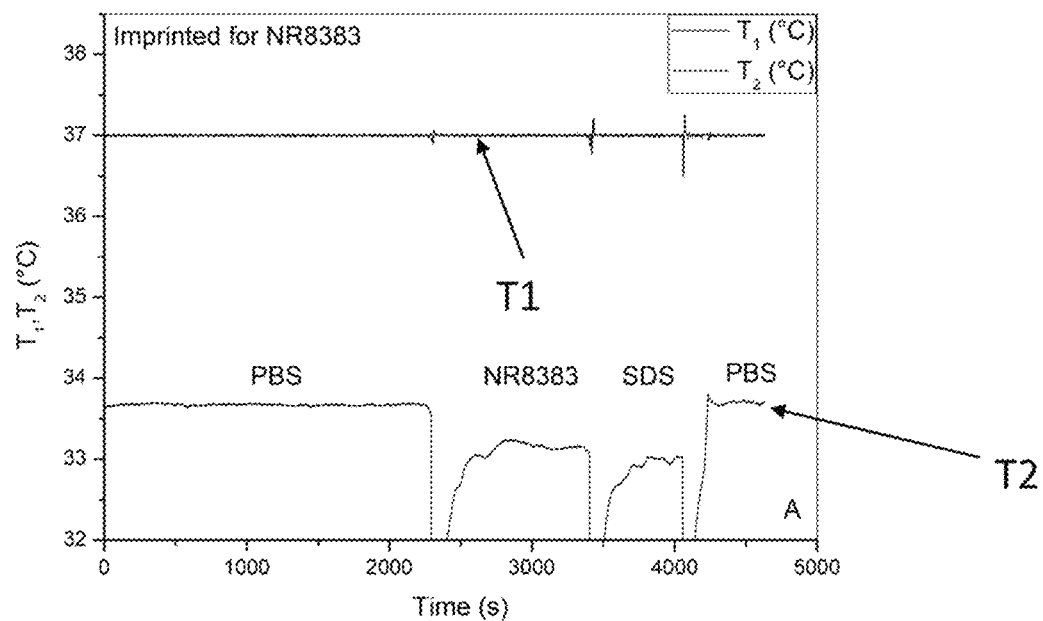
FIG. 4a illustrates the time dependence of a first temperature T1 of a copper block and a second temperature T2 of the liquid inside the flow-cell of the set-up, illustrating features of certain embodiments of the present invention.

The time dependence of T1 and T2 for a measurement run on an aluminum substrate 110 covered with a SIP imprinted for NR8383 is shown in FIG. 4a. The feedback from the PID to the adjustable heat source indeed ensured that T1 remains constant throughout the entire measurement. The temperature T2 reached a stable value after stabilization in buffer. Upon addition of the cells (1.106 cells/ml in PBS) T2 stabilized at a lower temperature in comparison to the plateau reached before addition. Flushing the system with 0.1% SDS solution did not cause a further drop in T2, however after rinsing the system again with the buffer solution PBS the temperature of the liquid reached the same value as in the first phase of the measurement, meaning the block on the heat-transfer was no longer present. The cells have been removed from their binding cavities.

Figure 4B:
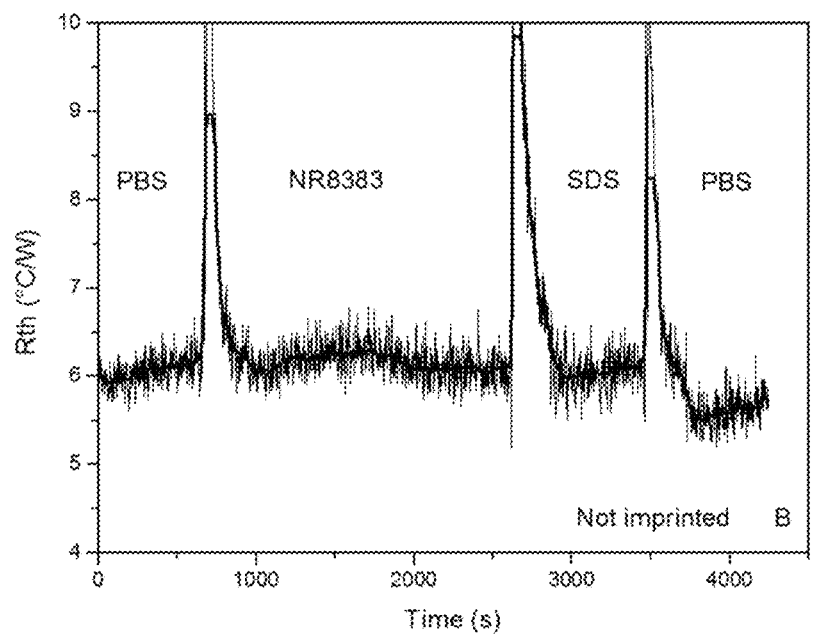
FIG. 4b illustrates a heat-transfer resistance $R_{th}$ as function of time, illustrating features of certain embodiments of the present invention.

To ensure specificity of our sensor platform the heat-transfer measurement was also conducted on aluminum substrates covered with NIPs. The NIPs, being made in exactly the same way as the SIPs but without the templating cell on the stamp during imprinting, was tested to ensure that the major part of the observed signal could be contributed to specific binding of the cells in the binding cavities of the SIP rather than to non-specific adsorption of the cells to the polymer layer. When analyzing the results summarized in FIG. 4b it becomes clear that the drop in T2 is absent after addition of the cells to the flow-cell and T2 remains constant throughout the entire measurement.

Figure 5A:
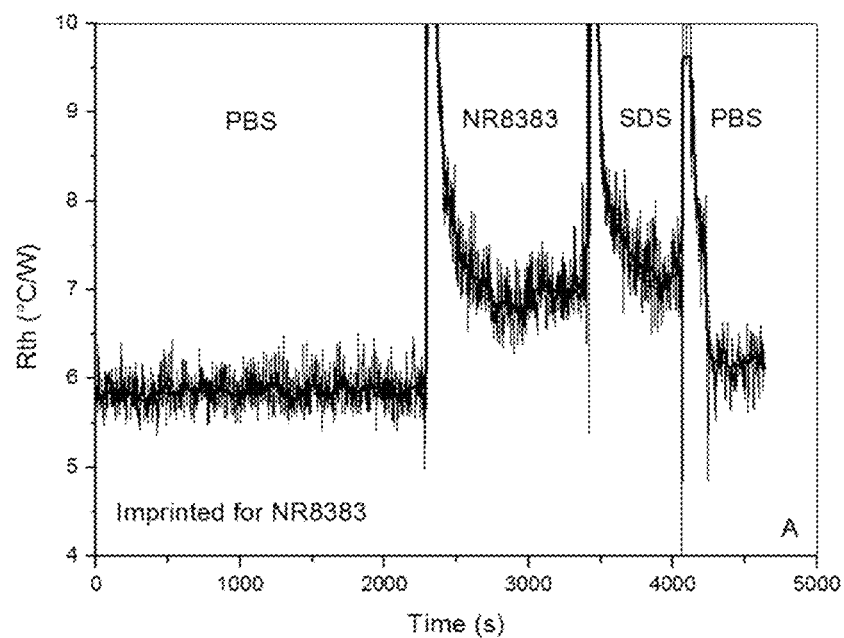
FIG. 5a illustrates heat-transfer resistance $R_{th}$ as function of time using a surface imprinted polymer (SIP), illustrating features of certain embodiments of the present invention.
Figure 5B:
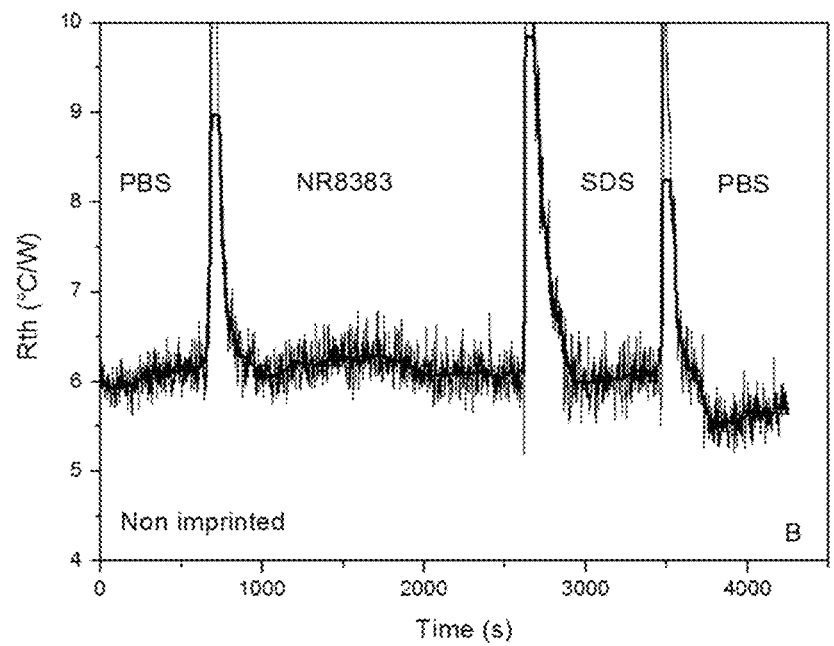
FIG. 5b illustrates heat-transfer resistance $R_{th}$ in function of time using a non-imprinted polymer (NIP), illustrating the characterisation limitations of prior art devices.

In order to get an indication about the exact resistance of the layer before and after addition of the target cells, it was not sufficient to solely analyze the time dependence of T1 and T2. The thermal resistance (Rth) can be calculated at any time during the measurement, using the following equation: $R_{th}=\Delta T/P$ with $\Delta T=T_1-T_2$ and P being the required heating power of the adjustable heat source needed to keep T1 constant at 37° C. The resulting data are shown in FIGS. 5a&b. The noisy appearance of the data is due to the fact that these are the raw data of the device. While T1 is kept fairly constant in almost a straight line during the measurements, the input power to the heat source needed to keep this T1 constant was fluctuating. This effect is enhanced by the fact that there is no active temperature control in the environment where the measurements are performed.

The time dependence of Rth for the SIP is summarized in FIG. 5A. The Rth stabilized in PBS at a value of 5.9+/−0.2° C./W and rose to 7.0+/−0.2° C./W upon addition of the target. This rise corresponds to an increase in Rth by 20%, whereby the effect is substantially higher than the noise on the signal (4%) and is therefore a substantial effect indicative of binding of the target cells into the binding cavities of the SIP. Moreover NR8383 cells have a diameter of 20-25 μm, corresponding to only a fraction of the distance of 3 mm between the two thermocouples in the set-up. In comparison the Rth of the NIP summarized in a time dependent manner in FIG. 5B doesn't show any substantial rise. The Rth stabilized at a value of 6.04+/−0.1° C./W rising to only 6.08+/−0.1° C./W, this rise of 0.04° C./W (0.7%) falls within the noise of the system (2.2%). The results of both panels in FIG. 5 combined show that the fall in T2 for the SIP shown in FIG. 4 is caused by the binding of the target cells to the SIP, leading to an increase in heat-transfer resistance. The finding that the NIP lacks this drop in T2 as well as a rise in Rth confirms that the effect for the SIP can be accounted for by the specific binding of the target cells into the binding cavities of the SIP rather than to a specific adsorption of the target cells onto the surface of the polymer.

To address selectivity of the SIPs, substrates covered with SIPs imprinted for NR8383 cells were tested for their reaction with RAW 264.7 macrophage cells and Saccharomyces cerevisiae yeast cells both in PBS solution. To compose a full cross-selectivity matrix additional SIPs were made using RAW 264.7 cells and Saccharomyces cerevisiae as templating cells. In each case a corresponding NIP was synthesized. Each of the SIPs was eventually tested for their target cell as well as for the analogous cell types. The results of these measurements are summarized in table 1.

The numbers in bold, in the table, show the response of the SIP to its target. For each target the Rth response is given as well as the relative response. These results show that there is a significant rise in heat-transfer resistance when adding target cells to their SIPs. The signal-to-noise ratio is minimum 5:1 for the least responsive SIP (polyurethane imprinted for Saccharomyces cervisiae responding to target). In contrast the response of the SIPs to the analogue cell types as well as the response of the NIPs to the different cell types is not significant. The response is in any of these cases lower or equal to the noise of the system. The results in this table clearly show a lack of cross-sensitivity of the proposed sensor platform. Furthermore it appears that the SIP showing the least coverage is the most responsive, while the most fully covered SIP is the least responsive.

| | Target Concentration | | | | | |
|---|---|---|---|---|---|---|
| | NR8383 $1.10^6$ +/− $8.10^4$ cells/ml | | RAW 264.7 $1.10^6$ +/− $9.10^4$ cells/ml | | Saccharomyces cerevisiae $1.10^6$ +/− $9.10^4$ cells/ml | |
| | ΔRth (° C./W) | % respons | ΔRth (° C./W) | % respons | ΔRth (° C./W) | % respons |
| Imprint: NR8383 7899 +/− 444 cavities/cm² | 1.14 +/− 0.2 | 19.5 +/− 3.5 | −0.18 +/− 0.1 | −2.8 +/− 2 | −0.18 +/− 0.04 | −3.1 +/− 0.7 |
| Imprint: RAW 264.7 21649 +/− 8758 cavities/cm² | 0.10 +/− 0.2 | 1.79 +/− 2.8 | 0.85 +/− 0.2 | 13.9 +/− 3.2 | 0.14 +/− 0.2 | 2.4 +/− 5.4 |
| Imprint: Saccharom. Cerivisiae 183221 +/− 54233 cavities/cm² | 0.01 +/− 0.2 | 0.19 +/− 3.1 | 0.14 +/− 0.1 | 2.29 +/− 2.1 | 0.55 +/− 0.1 | 9.65 +/− 2.6 |
| Non imprinted | 0.04 +/− 0.1 | 0.7 +/− 2.3 | 0.05 +/− 0.2 | 0.84 +/− 2.8 | 0.14 +/− 0.1 | 2.32 +/− 2.0 |

Dose-Response of an NR8383 Imprinted SIP

Figure 6A:
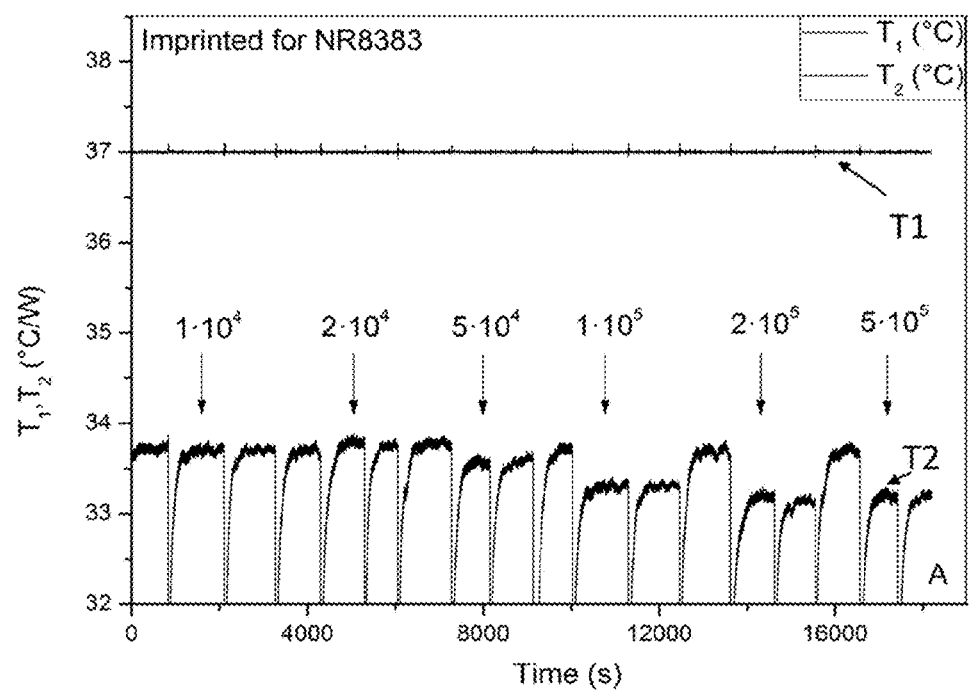
FIGS. 6a, b, and c illustrate a dose-response experiment conducted on a SIP imprinted for NR8383 cells, illustrating features of certain embodiments of the present invention.
Figure 6B:
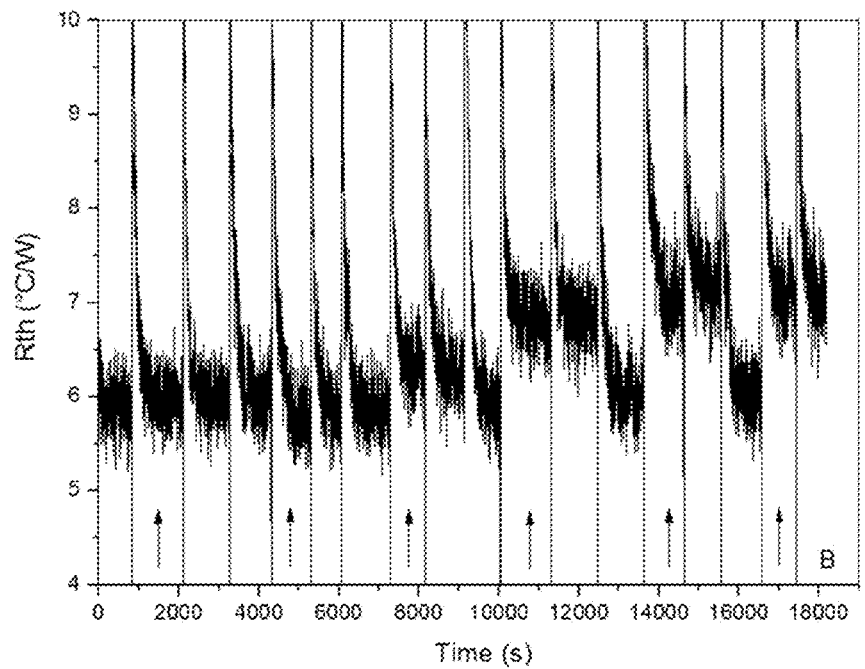
Figure 6C:
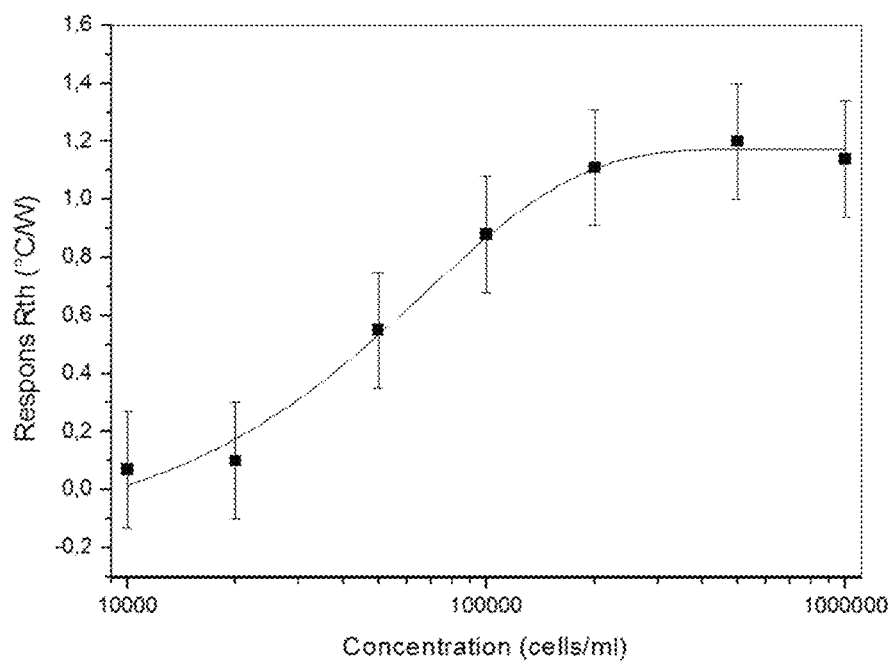
FIG. 6c illustrates a dose-response curve, response in $R_{th}$ in function of concentration of target cells added.

In previous captions experiments were conducted to assess whether it was possible to qualitatively detect various cell types. To determine if it was possible to quantitatively measure the concentration of a certain cell type in buffer solution, the response of a SIP imprinted for NR8383 cells (being the most responsive SIP) to a dilution series of NR8383 cells in PBS pH 7.4 was also examined. To this extend, the stock solution of NR8383 cells in PBS (concentration $1 \cdot 10^6$ cells/ml) was diluted 100, 50, 20, 10, 5 and 2 times. Prior to the measurements the system was stabilized in PBS pH 7.4, after addition of each concentration in the dilution series, the flow through cell was flushed with 0.1% SDS solution and PBS to ensure complete removal of any bound cells in the binding cavities of the SIP. The time dependence of T1 and T2 and the change in heat-transfer resistance Rth in function of time are summarized in FIG. 6a en FIG. 5b respectively. These figures show clearly that initially there is no response in T2 or Rth at low concentrations of cells. Increasing the concentration of cells added to the flow cell to $5 \cdot 10^4$ cells/ml causes a decrease in the temperature of the liquid T2. This temperature dip is due to the fact that the Rth rises with 0.55+/−0.2° C./W. Increasing the concentration leads to an increased effect on T2 and Rth. At a concentration of $1 \cdot 10^5$ cells/ml the system reaches saturation at a $\Delta R_{th}$ value of 1.1+/−0.2° C./W. The values obtained in the experiment were used to construct a dose-response curve shown in FIG. 5c. The concentration was transformed logarithmically and the response data in function of the concentration of target cells can be fitted exponentially. The curve shows a nice fit (R2=0.988), with no significant response at low concentrations, a stepwise increase in heat-transfer resistance at moderate concentration and leveling off at higher concentrations.

Proof of Application: Selective Detection of Human Cancer Cells

In order to assess whether the sensor set-up can also be used to detect biological relevant cells in a selective manner, SIPs were created for MCF7, a breast cancer cell line and Jurkat, an immortalized T lymphocyte cell line derived from a leukemia patient. To determine if the sensor was able to discriminate between a healthy cell and a cancerous cell, additionally a SIP was imprinted with peripheral blood mononuclear cells (PBMC's) of healthy human subject, consisting out of healthy T- and B-lymphocytes as well as monocytes and macrophages. The imprinting procedure as well as the heat-transfer measurements were done as described in earlier sections for the animal cells. The results are summarized in table 2.

targets falls within the noise of the system. The results also show that there is no cross-selectivity between the SIPs imprinted for MCF-7 cells and PBMC's, the response of the MIP to the analogue can be neglected in both cases. However there appears to be some cross-selectivity between MCF-7 and Jurkat, the two cancer cell types and between Jurkat and PBMC's, the two blood cell types. The response of a Jurkat SIP to both analogue cell types appears to be significantly higher than the noise of the system and can thus be regarded as significant. However the response of the SIP to its target is about 4 times higher compared to the response to the analogue cell types. The SIP imprinted for MCF-7 also shows a significant response to Jurkat cells, but the signal after addition of the target is 3.5 times larger as compared to the rise in Rth after addition of MCF-7 cells. When comparing the rise in Rth for a SIP imprinted for PBMC's, the effect of adding the target is about 2.5 times higher as compared to the effect of adding Jurkat cells to the SIP.

Enhancing the Selectivity of Cell Recognition

Figure 12A:
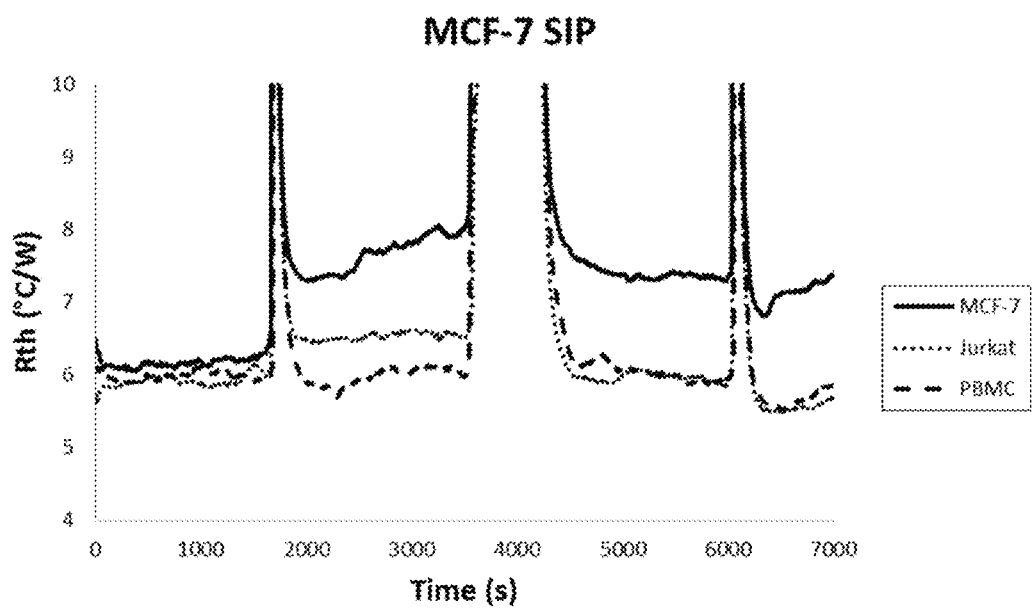
FIG. 12a to FIG. 12c illustrates measurement specificity for different materials using different imprints, illustrating features of certain embodiments of the present invention.

Based on the idea that a non-specific sensor response stems mainly from a simple geometrical matching between the cells and the imprints rather than from chemical interactions, a rinsing-based technique was developed for selectivity enhancement. The sensor setup was connected to a computer-controlled flow system, allowing administering cell suspensions and rinsing fluid (pure PBS) at defined moments with defined flow rates. FIG. 12a summarizes data obtained all with a single MCF-7 SIP layer: When MCF-7 cells are introduced at a rate of 2.5 ml/min (3 ml in total, 72 seconds), Rth increases from 6.0 to 7.5° C./W under static conditions. The flushed-in volume exceeds the initial PBS-filling of the liquid compartment by almost 30 times and Rth runs up to 8.0° C./W, possibly due to sedimentation effects on top of the specific recognition. A 'mild' rinsing step with cell-free PBS (flow rate 0.25 ml/min, total volume 3 ml, 12 minutes) brought the Rth response back to 7.5° C./W and this remained stable even after 'stringent' rinsing with the same PBS volume, now applied at a PBS flow rate of 2.5 ml/min during 72 seconds. Redoing this sequence with PBMC, the sensor base line at 6.0° C./W did not change over time. The same experiment with Jurkat cells gave a non-specific increase of 0.5° C./W after introducing the Jurkat solution, while already the first rinsing step re-established the base line and there was no further change after stringent rinsing. This means that the shear forces exerted by the liquid flow are sufficient to break the non-specific sticking

|  | Target Concentration | | | | | |
|---|---|---|---|---|---|---|
|  | MCF-7 $1 \cdot 10^6$ +/− $9 \cdot 10^4$ cells/ml | | Jurkat $1 \cdot 10^6$ +/− $7 \cdot 10^4$ cells/ml | | PBMC $1 \cdot 10^6$ +/− $1 \cdot 10^5$ cells/ml | |
|  | ΔRth (° C./W) | % respons | ΔRth (° C./W) | % respons | ΔRth (° C./W) | % respons |
| Imprint: MCF-7 | 1.09 +/− 0.1 | 18.0 +/− 2.1 | 0.33 +/− 0.1 | 5.0 +/− 2.3 | 0.02 +/− 0.1 | 0.4 +/− 1.7 |
| Imprint: Jurkat | 0.26 +/− 0.1 | 4.4 +/− 2.4 | 1.15 +/− 0.2 | 19.7 +/− 2.7 | 0.27 +/− 0.1 | 4.4 +/− 1.1 |
| Imprint: PBMC | −0.08 +/− 0.1 | −1.4 +/− 1.7 | 0.31 +/− 0.1 | 5.2 +/− 2.3 | 0.75 +/− 0.1 | 12.6 +/− 2.1 |
| Non imprinted | 0.05 +/− 0.2 | 0.9 +/− 3.0 | 0.08 +/− 0.1 | 1.3 +/− 3.0 | 0.07 +/− 0.1 | 1.2 +/− 1.8 |

For each SIP the response indicated in bold represents the response of the SIP to the target that was used for imprinting. These results show that the SIP imprinted for the PBMC's is the least responsive SIP, showing a signal-to-noise ratio of 7:1. The signal-to-noise ratio for the SIPs imprinted for MCF-7 and Jurkat show a significant higher signal-to-noise ratio of about 11:1. The response of the NIPs to all three between cells and imprints, which match only in size while missing chemical complementarities.

Figure 12B:
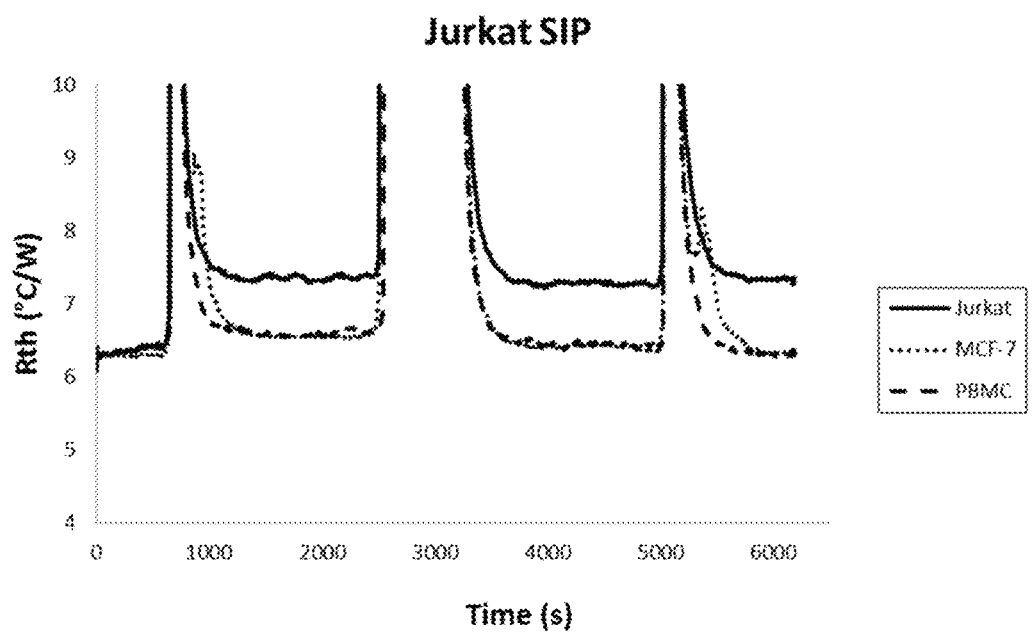
Figure 12C:
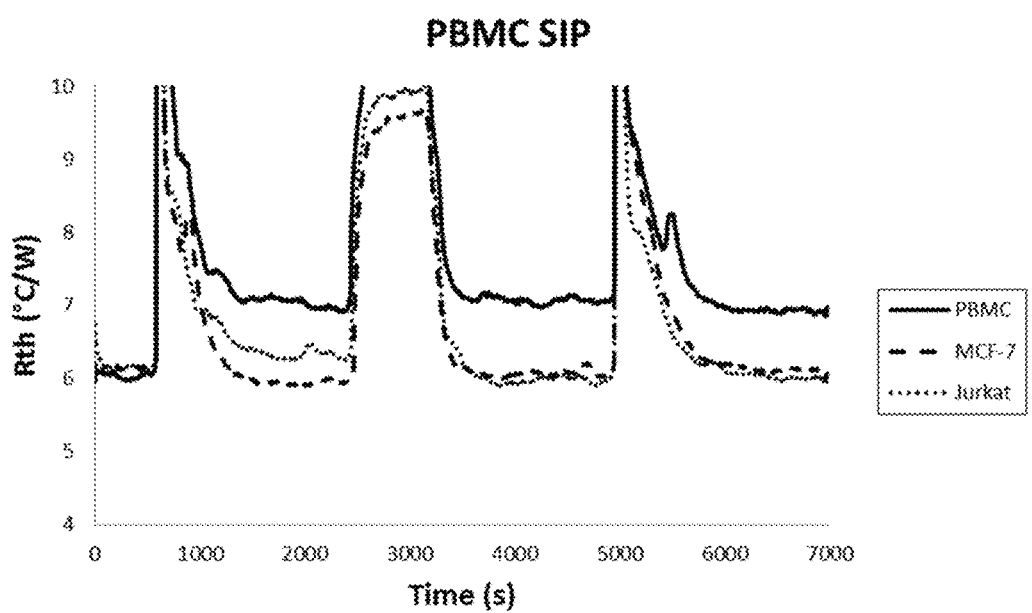
Figure 13A:
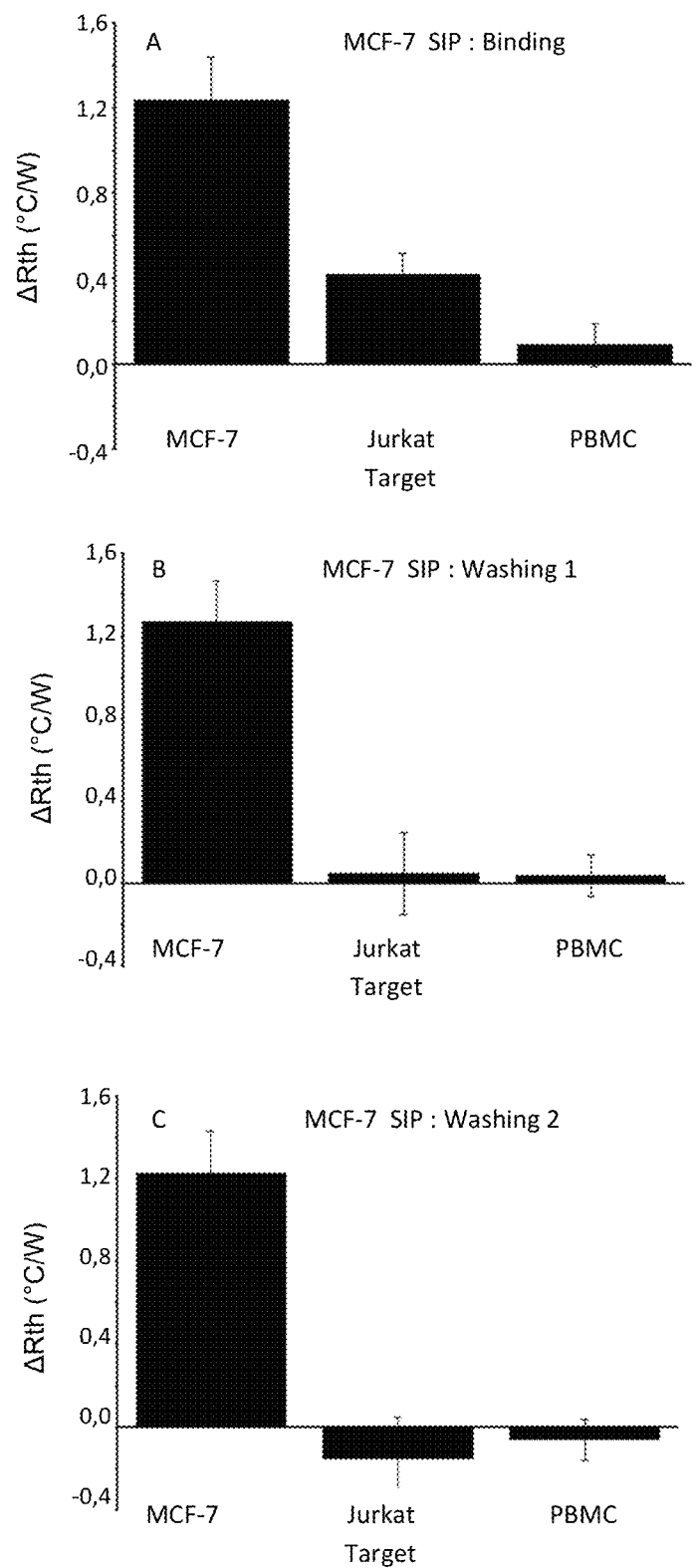
FIG. 13a to FIG. 13c illustrates binding- and rinsing data for a cross-selectivity matrix for experimental data obtained using devices according to certain embodiments of the present invention.
Figure 13B:
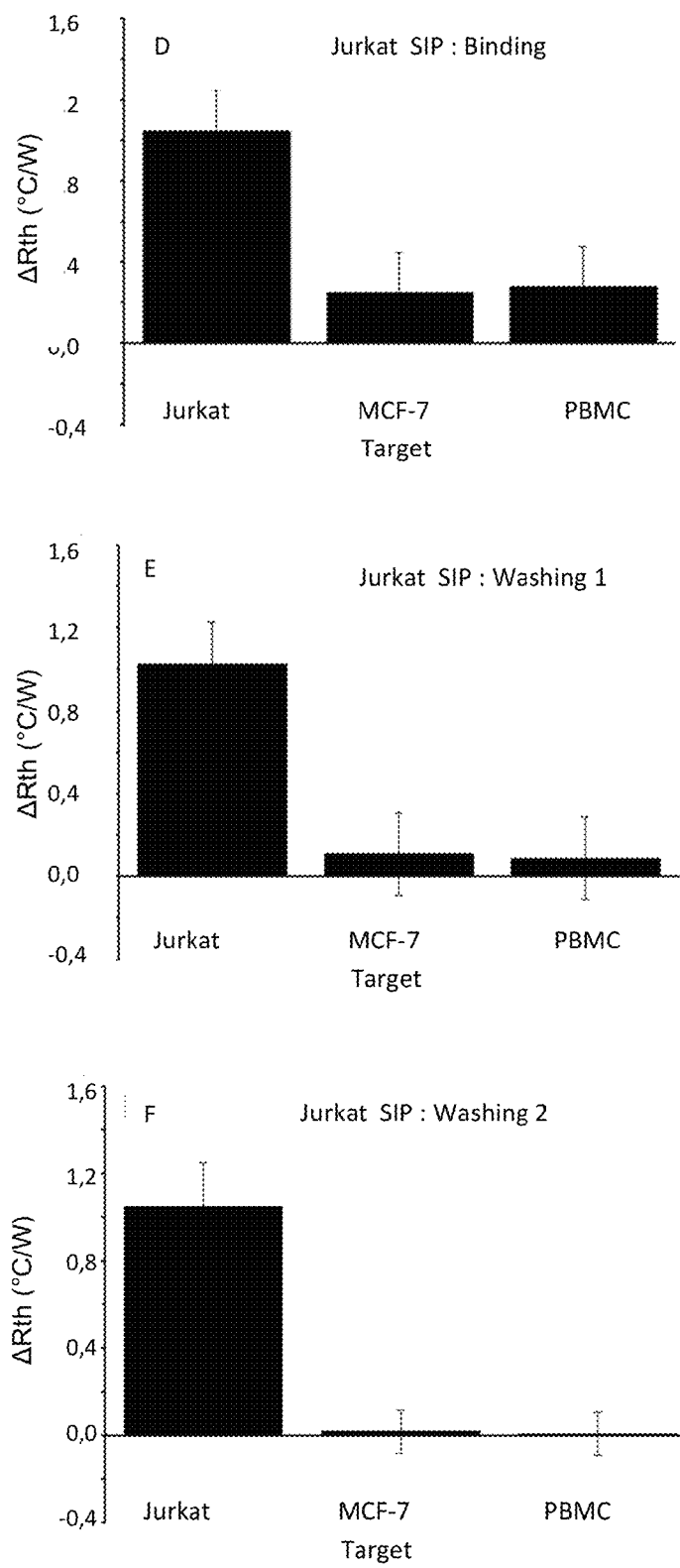
Figure 13C:
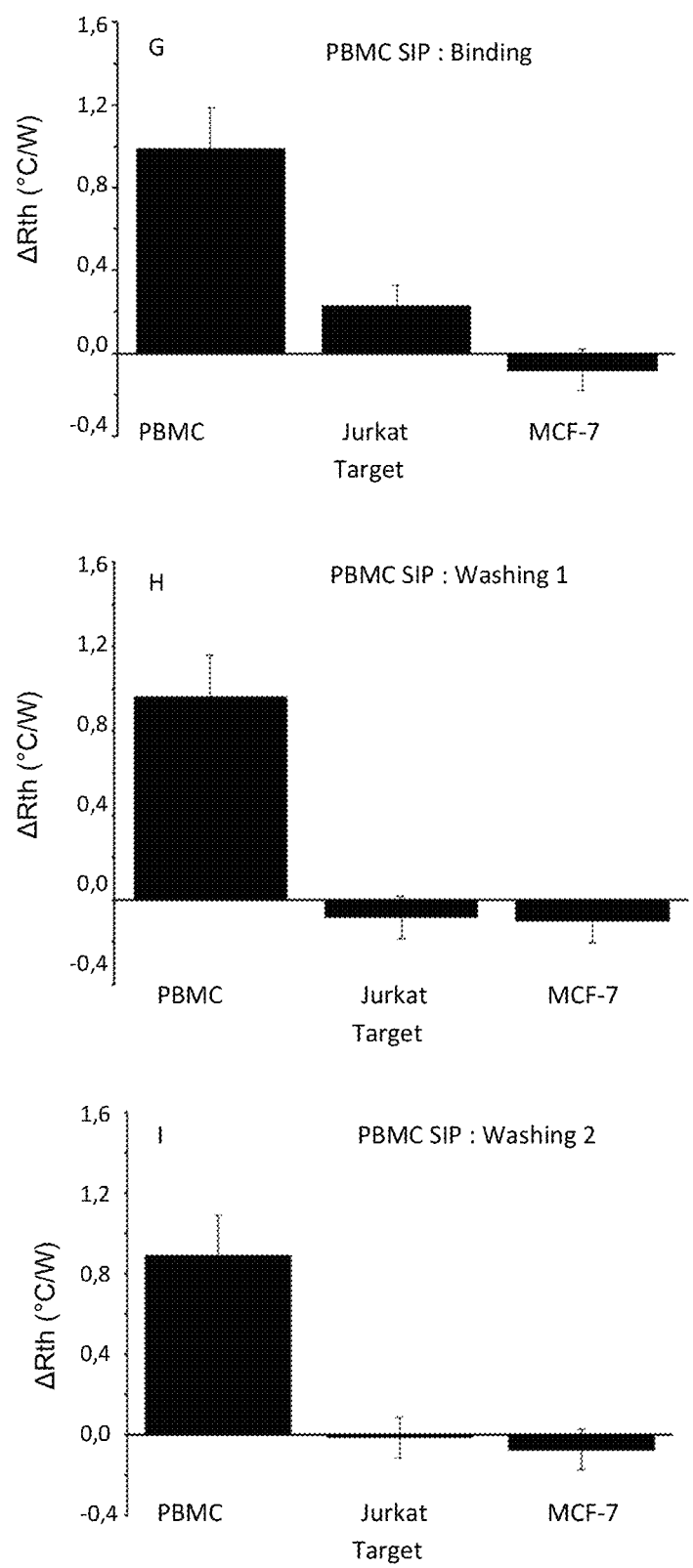

Repeating this experiment with a Jurkat-imprinted SIP layer (FIG. 12b) showed a selective, permanent recognition of Jurkat cells while the non-specific response to MCF-cells and PBMC (+0.5° C./W in both cases) vanished after rinsing. Similarly, also the non-specific response of Jurkat cells to PBMC imprints (+0.4° C./W) can be cancelled out by this method as shown in FIG. 12c. All binding- and rinsing data for the cross-selectivity matrix of the three different imprint types with the three types of target cells are condensed as bar charts in FIG. 13. The latest after the second, 'stringent' rinsing, the cross-response is smaller than the error bars defined by the noise level. At the same time, the Rth increase of SIPs, which have selectively rebound their template molecules, remains constant, demonstrating the efficiency of the rinsing-based selectivity enhancement.

Discussion

The above results illustrate features of embodiments of the present invention, whereby it is proposed to use heat-transfer resistance as a tool for the specific detection and quantification of cells. Embodiments of the present invention thereby can make use of a straightforward detection platform using only two thermocouples, a PID controller and an adjustable heat source in combination with a structured substrate. This way, the proposed platform is cheap, easy to use and easy to miniaturize in the future. The platform can also be applied in other fields.

Although it was reported earlier that there is an improvement in thermal conductivity in fluids comprising nanoparticles in comparison to fluids lacking the presence of these nanoparticles, no comparable effect of the presence of micro-size particles in liquid on the heat transfer resistance of the liquid could be established. Moreover, also measurements conducted on bare aluminum substrates and non-imprinted polyurethane layers on aluminum, did not show an effect on Rth upon addition of cells to the flow cell. Therefore, it was surprisingly found that an increase of the heat transfer resistance Rth can be used for detection or characterisation upon binding of micrometer sized cells to a structured layer, e.g. an imprinted polymer layer. The finding that binding of the cells to a synthetic receptor causes an increase of heat-transfer resistance cannot be explained by a calorimetric effect. Recently calorimetric sensors have been reported for the detection of phenylacetate with synthetic receptors. These sensors however measure an increase in thermal energy arising from the energy set free by the molecular recognition of a target by a molecular imprinted polymer. Without wishing to be bound by theory, the rise in heat-transfer resistance may be explained by the schematic drawing in FIG. 3b. The detection may be based on specific binding of the target cells to the surface imprinted polyurethane as non-imprinted polyurethane layers as well as blank aluminum substrates do not show an increase in Rth upon addition of cells to the flow cell. The complementarity of the binding cavities to their target may furthermore not only be based on size and shape but also on the distribution of functional groups on the surface of the target cell. The latter is supported by an additional experiment done with imprinting a polyurethane layer for silica beads, where it was concluded that the rise in thermal resistance is accounted for by the binding of the target into the binding cavity. This causes a thickening of the thermal insulating layer, measured as an increase in thermal resistance.

With the present example, it is clearly demonstrated that the sensor set-up is able to distinguish between two different cancer cell lines and a negative control (PBMC). The slight cross-selectivity between the SIPs imprinted for PBMC and Jurkat is not surprising, as Jurkat cells are an immortalized T-cell line and PBMC's consist partly of healthy T cells. The fact that in the example an excess of cells was used for the measurements results in healthy T cells binding to binding cavities imprinted for Jurkat cells and vice versa. The fact that there is also some crosstalk between the SIPs imprinted for Jurkat and MCF-7 is somewhat remarkable but probably originates from the fact that cancer cells from different nature do have similar membranes. Certain proteins on the membrane of cancer cells, such as the MUC1 protein, promote cancer development and result in cross selectivity of imprinted polyurethane layers. However in all the observed cases the effect of binding of a target to its SIP is several times higher in comparison to rise in Rth observed after adding an analogue cell type and can therefore easily be distinguished using embodiments of the present invention. The specific and selective detection of cancer cells using the concept of structural imprinting of polyurethane in combination with thermal resistance measurements according to embodiments of the present invention may provide a novel and revolutionary tool in cancer research. The method and device according to embodiments of the present invention show comparable results compared to amperometric, magnetoelastic or microgravimetric techniques and using impedance spectroscopy and optical sensor while embodiments of the present invention can make use of a low-cost set-up platform.

Design of the Sensor Set-Up

The polyurethane-covered aluminium substrates were horizontally mounted in a home-made flow cell of 110 µl. The substrates are fixed onto the copper backside contact of the device by use of four small screws. Silver paste is used to ensure good thermal contact between the copper and the aluminum. Liquids were exchanged using a syringe-driven flow system (ProSense, model NE-500, The Netherlands). All measurements described were performed under static conditions. Two miniaturized thermocouples (type K, diameter 500 µm, TC Direct, The Netherlands) were used for monitoring the temperature T1 of the copper backside contact and the temperature of the solution in the flow cell T2 at 1.7 mm above the chip surface in the center of the flow cell. Heat flow was generated with a power resistor (22, MPH20, Farnell, Belgium) attached to the copper block using heat-conductive paste and tightly fixed with a screw. The thermocouple signals were led to a data acquisition unit (Picolog TC08, Picotech, United Kingdom) and was further processed into a PID controller (parameters: P=10, D=50, I=0.1), in this way T1 is regulated. The output voltage calculated by the PID controller was fed back into the power resistor via a second controller (NI USB 9263, National Instruments, USA) and a power operational amplifier (LM675, Farnell, Belgium). The sample rate of the T1 and T2 values was 1 measurement per second.

Imprinting Protocol for the Synthesis of Surface Imprinted Polyurethane Layers

The reagents were used as received. Polyurethane layers were formed by dissolving 122 mg of 4,4'-diisocyanatodiphenylmethane (Sigma), 222 mg of bisphenol A (Sigma) and 25 mg of phloroglucinol (Sigma) in 500 µl of anhydrous tetrahydrofuran (THF). The mixture was stirred at 65° C. for 200 minutes under inert gas until the polymer solution reached the gelling point. The solution was diluted 1:5 and spin-coated at 2000 rpm onto 1 cm2 aluminium substrates.

In parallel home-made poly dimethyl siloxane (PDMS) stamps were covered with cells in order to stamp the cells into the spin-coated polyurethane layer. PDMS stamps were made using the 184 silicone elastomer kit (Sylgard). Several hundreds of microliters of cell suspension in PBS were applied to the PDMS stamp. After 50 seconds of sedimentation time, the excess fluid was removed by spinning at 3000 rpm in order to create a dense monolayer of cells on the stamp surface.

The cell-covered stamp was gently pressed into the polyurethane layer and cured overnight at 65° C. under inert atmosphere. After curing, the stamp was removed from the surface. By rinsing the surface with 0.1% sodium dodecylsulfate solution and PBS, the templating cells were removed from the polymer, leaving behind specific binding cavities on the polyurethane surface.

Non-imprinted polymer layers, used for assessing specificity, were made exactly the same as their imprinted counterparts. However, the stamp was not covered with target cells in this case and the layers could be used for reference purposes.

Culturing of the Cells

Mouse leukaemic monocyte macrophage RAW 264.7 cells (ATCC: TIB-71), rat alveolar macrophage NR8383 cells (ATCC: CRL-2192) and Jurkat cells (ATCC: TIB-152) were cultured in Roswell Park Memorial Institute medium (RPMI medium, Lonza). Cells were passaged at a confluence of about 80%. Prior to imprinting and measurements, the RPMI medium was exchanged with phosphate bufferd saline (PBS) in six washing steps in order to remove proteins of the culture medium. *Saccharomyces cerevisiae* solutions were made by dissolving compressed baker's yeast from Dr. Oetker in PBS buffer solution. Cell counting for determining buffer concentrations was done using a haemocytometer.

MCF-7 cells (ATCC: HTB-22) were cultured in Eagle's Minimum Essential Medium (EMEM medium, Lonza). And were passaged and washed as described above for other cell types. Peripheral blood mononuclear cells were isolated from blood samples of a healthy subject using a ficoll separation technique. In order to remove unwanted proteins from the medium the cells were washed with PBS in three steps.

Surface Characterization of SIPs

Optical analysis of the imprinted polyurethane layers was done using an Axiovert 40 inverted optical microscope (Carl Zeiss). Atomic force microscope measurements in contact mode were performed with a Digital Instruments nanoscopeIIa multimode SPM (Veeco) using a PPPNCHR cantilever and Aluminum reflex coated silicone probes (Veeco) in order to obtain depth profiles of the imprints.

Example 2

Molecular Imprinted Polymers

General Concept of the Device for Specific Measurements of Target in Buffer

The general principles of the heat-transfer device are shown in FIG. 2. The MIP and NIP particles are immobilized into a conductive polymer layer. With optical microscopy in combination with image, the MIP (25%±2) and NIP (24±3) were found to have identical particle loadings which is necessary to perform differential measurements.

Molecularly Imprinted Polymers (MIPs) can rebind their templates in a specific and selective manner due to non-covalent interactions between target and functional monomers. The synthesis is schematically described in FIG. 7. After polymerization and extraction, nanocavities are obtained with affinity for the template based on size and functionality. Upon rebinding, heat transport is blocked in that direction resulting in a total increase in the total heat-transfer resistance.

The MIP- and NIP functionalized aluminum substrates were mounted into the flow-cell, which was subsequently filled with phosphate buffered saline (PBS) of pH 7.4. The temperature of the copper, $T_1$, was strictly controlled at 37±0.02° C. by the PID controller. When $T_2$ reached a stable level, increasing concentrations of L-nicotine in PBS (0.2-25 µM) were added. Between each addition, the sensor was left to stabilize for at least 15 min. The time-dependence of $T_1$ and $T_2$ for a measurement with the MIP functionalized electrode are shown in FIG. 4a.

Figure 7:
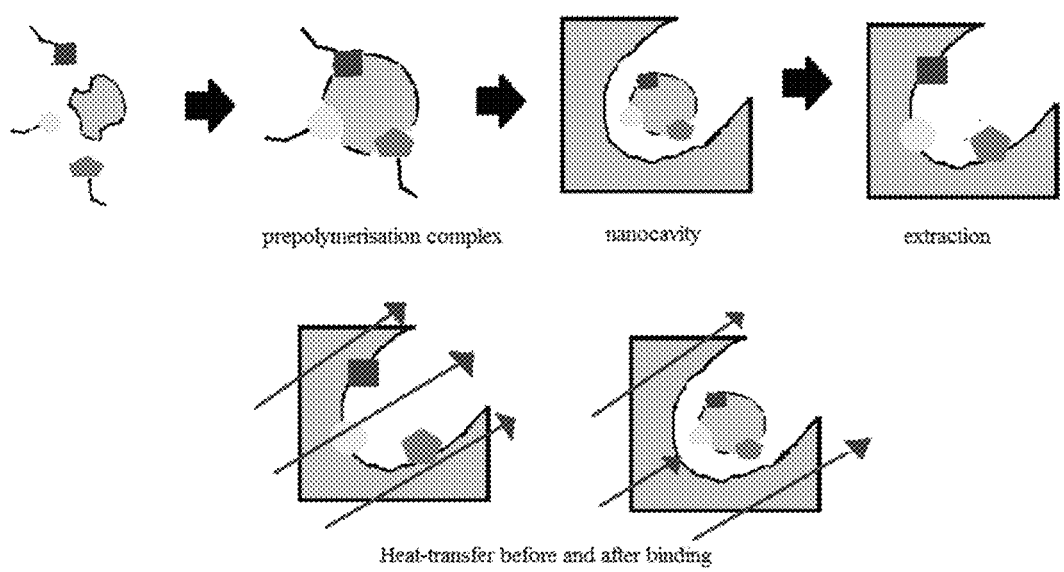
FIG. 7 illustrates the synthesis of a molecularly imprinted polymer (MIP) in a schematic way, illustrating features of certain embodiments of the present invention.
Figure 8A:
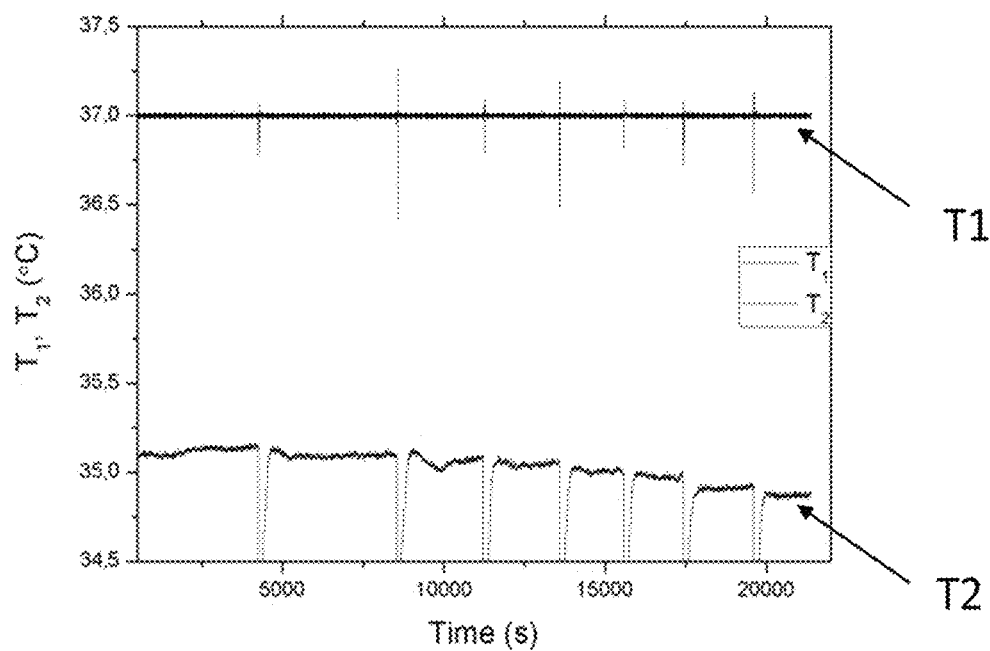
FIG. 8a illustrates heat-transfer resistance $R_{th}$ in function of time using an MIP, illustrating features of certain embodiments of the present invention.
Figure 8B:
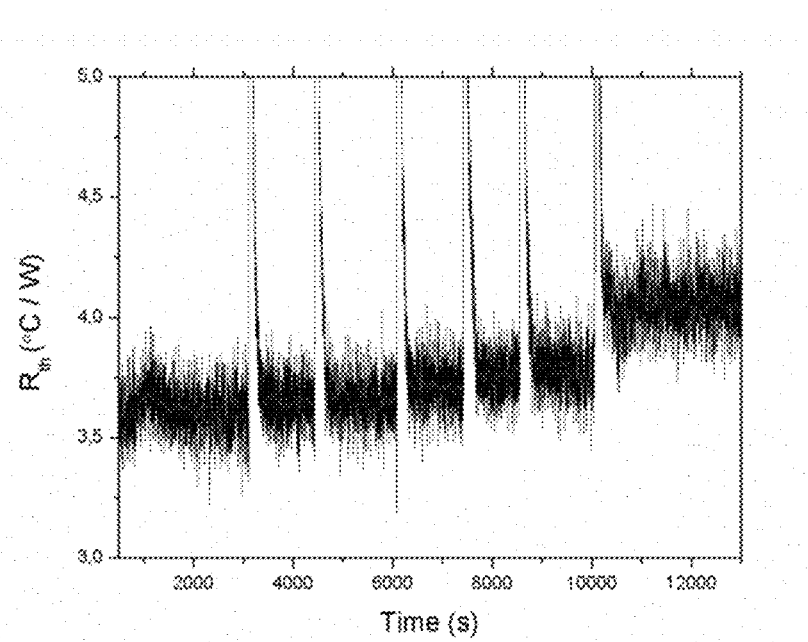
FIG. 8b illustrates heat-transfer resistance $R_{th}$ in function of time using a non-imprinted polymer, illustrating features of certain embodiments of the present invention.
Figure 9:
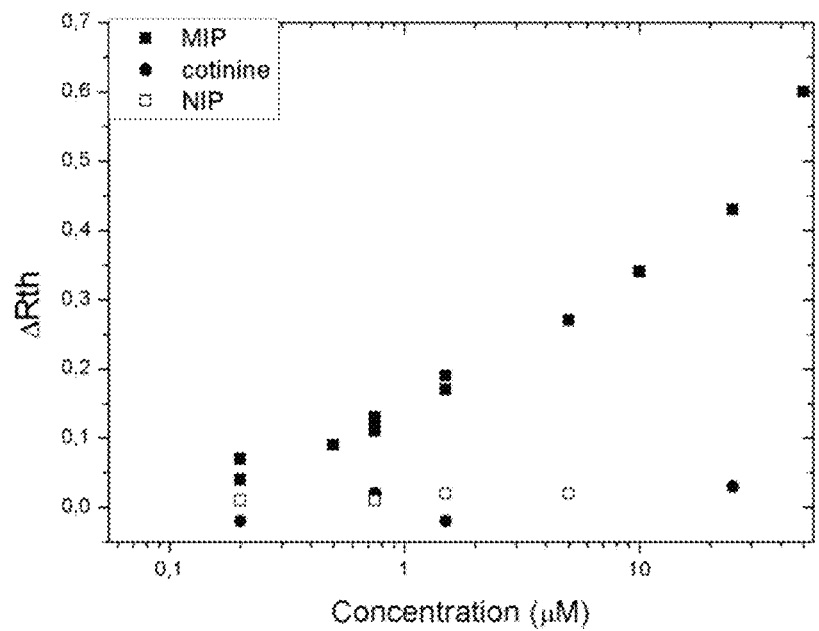
FIG. 9 illustrates a dose-response curve for a MIP, NIP and MIP with cotinine, illustrating features of certain embodiments of the present invention.

From FIG. 4a is directly clear that upon flushing with L-nicotine concentrations higher than 0.2 µM, a drop in $T_2$ is observed while $T_1$ remains constant. This can be explained by the block of the heat-transfer caused by the binding of the L-nicotine in the nanocavities of the MIP (FIG. 7). The higher the concentration of L-nicotine is, the more will be bound resulting in an increased effect on the heat-transfer.

To analyze the layer resistance before and after binding of the target exactly, it is not sufficient to solely determine the time dependence of $T_1$ and $T_2$. The thermal resistance ($R_{th}$) which is defined: $R_{th} = \Delta T/P$ was investigated. In this formula, $\Delta T$ corresponds to $T_1 - T_2$ and P the required heating power of the adjustable heat source in order to keep $T_1$ constant. With these parameters, the time dependence $R_{th}$ data was calculated for the MIP measurement.

In PBS, the $R_{th}$ stabilizes at 3.6±0.1° C./W and increases to 4.1±0.1° C./W upon addition of 5 µM of L-nicotine. The effect size of 14.0% is significantly higher than the noise on the signal (3%), thereby directly proving the binding of the target to the nanocavities of the MIP. These experiments were now repeated for the MIP with concentrations between 0.2-25 µM L-nicotine in PBS. In order to demonstrate specificity of the sensor platform, the same measurements were conducted on the NIP. Additionally, the effect of cotinine additions on the MIP was investigated. This was done in order to address the selectivity, as cotinine is similar in chemical structure and L-nicotine's natural metabolite. The $R_{th}$ data can be represented as a dose-response curve, where the difference in $R_{th}$ versus the concentration of the target is plotted. These results are illustrated in FIG. 5.

The MIP measurements were repeated three times. The average $\Delta R_{th}$ increase at a concentration of 0.75 µM was 0.12±0.01° C./W, showing excellent reproducibility of the samples. A detection limit of 0.2 µM ($\Delta R_{th}$=0.07±0.01) was achieved and we could measure up till a concentration of 50 µM ($\Delta R_{th}$=0.6±0.03). This is very interesting for biological measurements, for instance it covers the entire physiologically concentration range in saliva varying from negligible for non-smokers to 2-6 µM directly after cigarette consumption. The sensing platform was also determined to be specific and selective, as the $R_{th}$ remained constant during the measurement performed with the NIP and the MIP with cotinine. Simultaneously with the heat-transfer, impedance signals were measured which can be used as a validation technique.

Validation by Impedance Spectroscopy

The response of the MIP to L-nicotine in PBS has been previously investigated with an open addition set-up coupled to a commercial impedance analyzer. The closed flowcell as used here has the benefits of an integrated heating element and higher measuring speed, with only 5.7 s per sweep from 100 Hz to 100 kHz.

Figure 10:
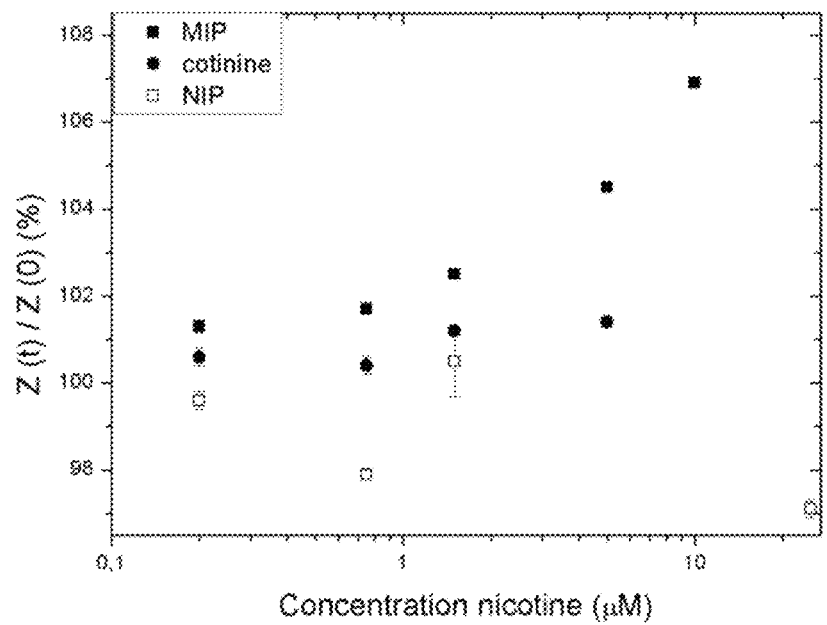
FIG. 10 illustrates dose-response curve at 316 Hz for a MIP, NIP and MIP with cotinine, illustrating features of certain embodiments of the present invention.

The MIP and NIP samples and L-nicotine and cotinine concentrations were prepared in the same way as for the heat-transfer measurements. After stabilization with PBS, increasing concentrations of L-nicotine and cotinine were added (0.2-25 µM). Between the addition steps the sensor was left to stabilize for 10 min. Subsequently, the response value was obtained by averaging five impedance data points with an interval of one minute. All the obtained impedance data were normalized with respect to a starting value of 100% pure PBS. The corresponding dose-response curves at a frequency 316 Hz are shown in FIG. 10. This frequency was selected because it is low enough to probe capacitive effects and ensures a high signal to noise ratio.

The MIP measurement showed an increase of 6.9±0.1%, while there was almost no change for the NIP and with the analogue cotinine there was only a minor difference of 1.4±0.1%. This corroborates the heat-transfer results, validating that the sensor platform is indeed useful for the specific and selective binding of L-nicotine. However, it is pointed out that the heat-transfer analysis is more straightforward and requires no additional mathematical operations.

Proof of Application: Detection of L-Nicotine in Saliva

Figure 11A:
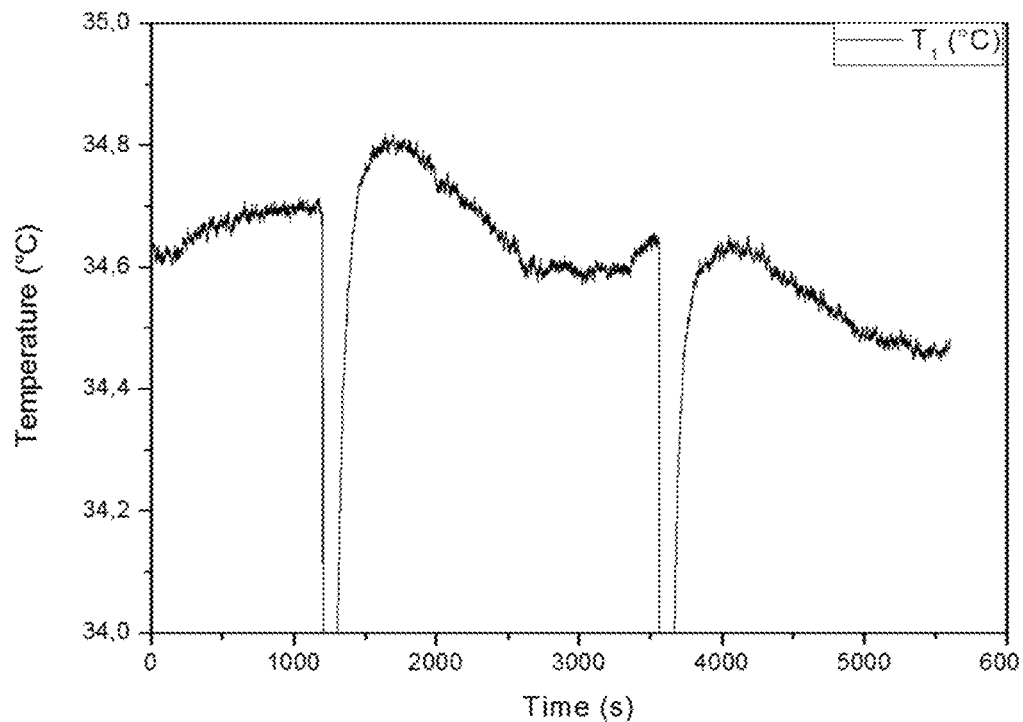
FIGS. 11a, b, c and d illustrate the time dependent behavior of T1 and T2 with saliva as stabilization step, the first addition was saliva collected after chewing nicotine gum (nicotine content 2 mg) and the second addition step was saliva obtained after chewing nicotine gum (nicotine content 4 mg) for MIP (FIG. 11a) and NIP (FIG. 11b), illustrating features of certain embodiments of the present invention. The corresponding Rth data are also shown for MIP (FIG. 11c) and NIP (FIG. 11d).
Figure 11B:
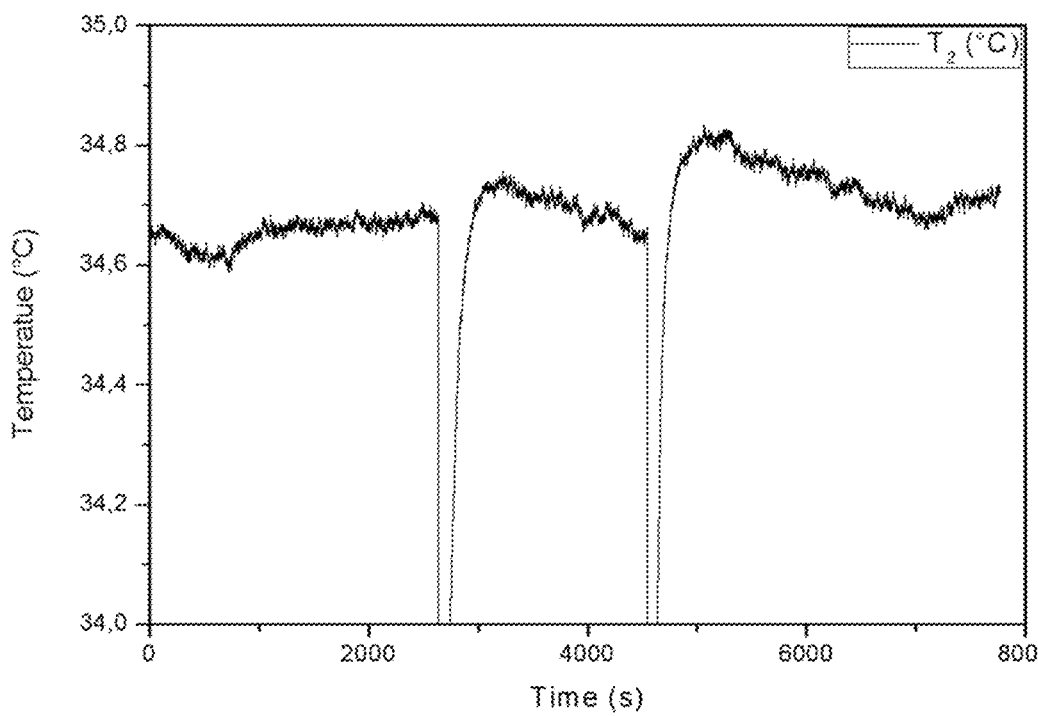
Figure 11C:
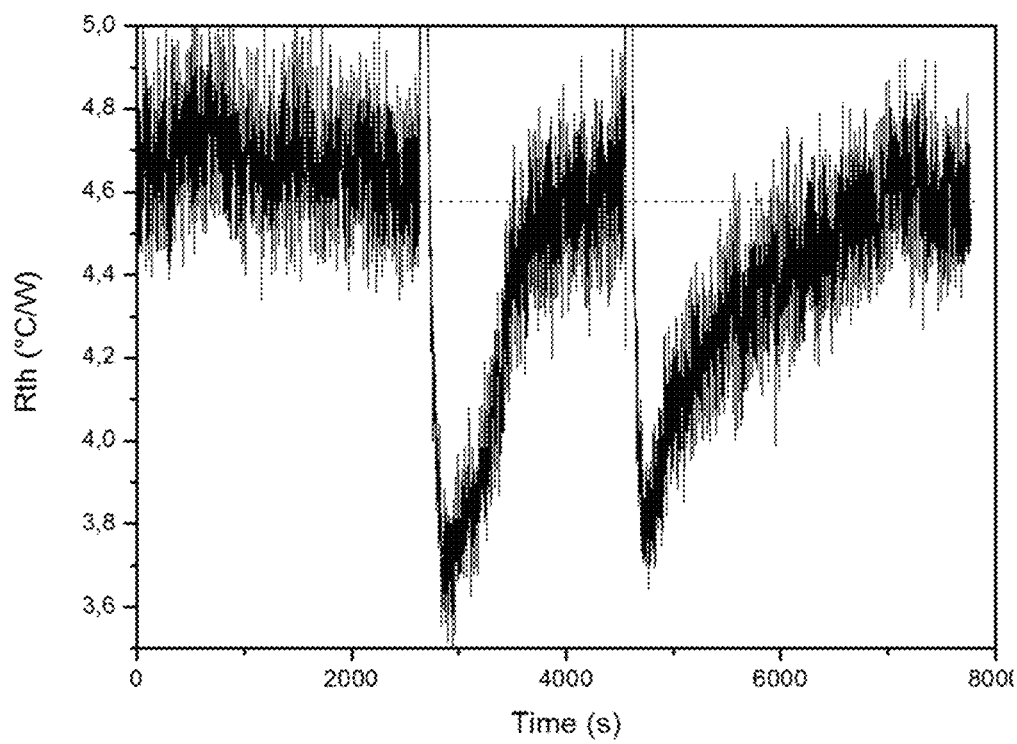
Figure 11D:
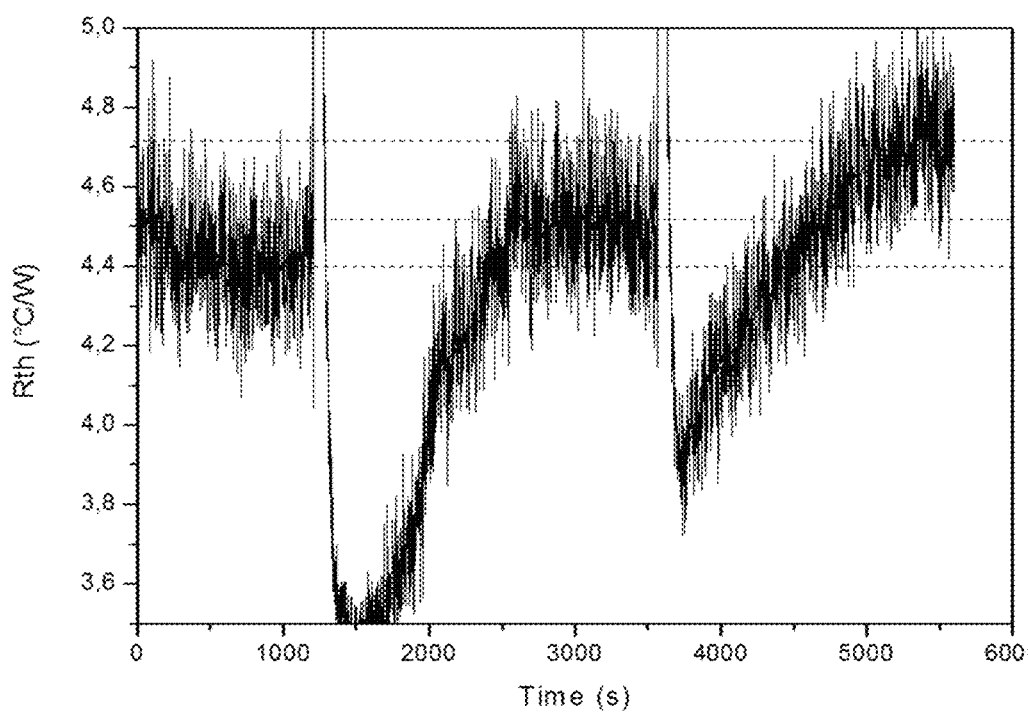

In order to assess the possible application for the sensor platform in biological media, saliva samples were investigated. First, a calibration curve was constructed with spiked concentrations of L-nicotine in saliva. The time dependent behavior of T2 and the Rth are shown in FIG. 11a and FIG. 11b for both MIP and NIP. When the saliva of a test person is added after chewing gum with a nicotine content of 2 mg, for the MIP a slight drop in T2 (0.1° C.) was observed. Upon adding saliva where the nicotine concentration in the chewing gum was twice as high (4 mg), the decrease in T2 (0.25° C.) is more pronounced. The same measurement performed with the NIP showed no difference in T2. FIG. 11c and FIG. 11d also shows the Rth data of MIP and NIP. For the MIP, the Rth stabilizes at 4.4±0.1° C./W which is slightly higher compared to the measurements performed in buffer (3.6±0.1° C./W). This was also the case for the NIP, stabilizing at 4.6±0.1° C./W. A possible explanation for this could be the higher viscosity of the saliva compared to buffer solutions. This can influence heat transport and also caused the slightly delayed response time.

For the buffer measurements, impedance spectroscopy can be directly used as validation technique. Impedance spectroscopy was applied previously for measuring biological samples such as plasma and bowel fluid, the saliva however was too viscous which resulted in an extremely high electrical resistance beyond the measuring limit. Thereby, results were verified with the Quartz Crystal Microbalance (QCM). For the QCM measurements, the samples first had to be severely diluted (0.125 ml in 19.88 ml of de-ionized H2O). By multiplying the response to the dilution factor, an estimate was made of the L-nicotine concentration equal to approximately 50 μM.

Design Sensor Setup

The aluminum substrates, functionalized with MIP and NIP particles, were horizontally mounted into a Perspex flowcell with an internal volume of 110 μl. Silver paste ensured good thermal contact between the copper and the substrate. Two miniature thermocouples (type K, diameter 500 μm, TC Direct, the Netherlands) monitored with a sample rate of 1 measurement per second temperature T1 of the copper backside contact and the temperature of the fluid, T2, 1.7 mm above the chip surface. Temperature T1 was strictly controlled to be 37±0.02° C. with a home-made PID controller (parameters: P=10, D=50, I=0.1). Hereby, the temperature inside the human body is mimicked. For the generated heat flow, a power resistor (22Ω, MPH20, Farnell, Belgium) was used which was attached to the copper block with heat-conductive paste. Simultaneously with the temperature, the impedance response were measured in a frequency range of 100 Hz to 100 kHz with 10 frequencies per decade and a scanning speed of 5.7 s per sweep. The amplitude of the AC voltage was fixed to 10 mV under open circuit conditions. All measurements were performed under static conditions.

Synthesis of Molecularly Imprinted Polymers and Preparation Electrodes

The MIP for nicotine was synthesized as follows: First, a mixture of 12.5 mmol MAA (Acros), 72 mmol EGDM (Acros) and 0.61 mmol AIBN (Fluka) was dissolved in 7 ml hexane together with 6.41 mmol of the template molecule L-nicotine (Acros). The solution was degassed with N2 and polymerized in a thermostatic water bath at 60° C. for 72 h. After polymerization, the polymer was ground and the L-nicotine was removed by Soxhlet extraction with methanol (48 h), a mixture of acetic acid/acetonitrile (1/1) (48 h) and again methanol (12 h). A non-imprinted polymer (NIP) was synthesized according to the same procedure, but without the presence of the target molecule. For the thermal and impedance measurements, 1×1 cm2 aluminum substrates were spincoated with conductive OC1C10-PPV. This PPV derivative, serving as an immobilization layer, was synthesized via the sulfinyl precursor route. Subsequently, MIP- and NIP particles were applied to the surface with a polydimethylsiloxane (PDMS) stamp. By heating the layer above its glass transition temperature, the powder was embedded into the layer. To ensure an equal load of the MIP- and NIP electrode, the sensor surface was studied with an Axiovert 40 inverted optical microscope (Carl Zeiss).

Preparation of Nicotine Samples

For a proof of principle, L-nicotine detection was performed in PBS buffer (pH=7.4). PBS buffer was used to simulate the ionic strength of biological samples. The L-nicotine concentrations were varied from 100 nM to 1 mM, ensuring the investigation of a large concentration regime. To test the selectivity, the same concentrations were prepared for cotinine in PBS.

As a next step, saliva samples were investigated. To collect the saliva, a non-smoker test person deposited saliva in a sterilized Falcon tube. The saliva was centrifuged immediately for 10 min with a speed of 10,000 rpm and the supernatant subsequently filtered with a 1 μm syringe filter. The obtained saliva sample were split into several aliquots. One aliquot was kept unaltered, thereby serving as a control fluid. The other aliquots were spiked with L-nicotine concentrations of 100, 500, 750, 1000 and 5000 μM. With this constructed dose-response curve, the concentration of L-nicotine in saliva samples after chewing nicotine gum was investigated. For obtaining these samples, the same test person chewed nicotine gum of different concentrations (2 and 4 mg L-nicotine of Nicorette® by Johnson and Johnson NV, Belgium) for 1 h, meanwhile collecting saliva in a sterilized Falcon tube. The saliva was then again centrifuged and filtered before measuring with the sensor platform.

Whereas various embodiments of the present invention have up to now been described with reference to heat transfer resistivity measurements, the present invention in another aspect also relates to embodiments based on impedance measurements using the same structured substrates as described above. More particularly, the present invention also relates to a method for characterising a target bioparticle, the method comprising obtaining a structured substrate having a surface comprising a plurality of binding cavities in which the target bioparticle can be bound, contacting said structured substrate with said target bioparticles and an electrolytic solution having a neutral pH in a flow cell and measuring a first impedance value within said electrolytic solution, and then inducing a release of the target bioparticles from the binding cavities and then measuring a second impedance value within the flow cell after completion of the release of the bioparticles, and then obtaining a value representative for the impact of the release induction on the impedance of the electrolytic solution, and then deriving, based thereon, a characteristic of the target bioparticles. Furthermore, the invention also relates to a bio-sensing device suitable for characterising a target bioparticle, the device comprising a flow cell equipped with an impedimetric analyzer, a structured substrate having a surface comprising a plurality of binding cavities in which the target bioparticle can be bound, exposed by at least the surface comprising the plurality of binding cavities of said substrate to the flow cell, a pumping system and switching valve connected to said flow cell, a first liquid supply comprising a electrolytic solution connected to said pumping system and switching valve, a release inducing means for releasing the bioparticles from the binding cavities, and a means for obtaining a value representative for the impact of release inducing means on the impedance of the electrolytic solution, and a means for deriving, based thereon, a characteristic of the target bioparticles. The release inducing means may be a second liquid supply for adding to said electrolytic solution a component inducing the release of the bioparticles from the binding cavities. It will be clear to the skilled person that for these aspects further features of embodiments of the present invention may be similar to those as described in embodiments described in the first or the second aspect of the present invention.

The invention claimed is:

1. A bio-sensing device suitable for the detection and/or characterization of target bioparticles, the target bioparticles not being DNA bioparticles or RNA bioparticles, the bio-sensing device comprising:
   a heating element configured to heat using a power;
   a sample holder comprising a structured substrate having a surface comprising a plurality of binding cavities in which the target bioparticles can bind, the sample holder further being adapted for exposing the structured substrate at one side to the heating element;
   a first temperature sensor configured to sense a temperature at the side where the structured substrate can be exposed to the heating element and a second temperature sensor configured to sense a temperature at the side opposite thereto with respect to the structured substrate;
   a processing means programmed for calculating at least one heat transfer resistivity value based on temperature values obtained with the first temperature sensor and the second temperature sensor and the power for the heating element, the heat transfer resistivity value being defined as $\Delta T/P$, in which P is the power of the heating element and $\Delta T$ is the difference between the temperature value of the first temperature sensor and the temperature value of the second temperature sensor, for deriving a characteristic of the target bioparticles from said heat transfer resistivity value.

2. A biosensing device according to claim 1, wherein the structured substrate is an imprinted substrate.

3. A biosensing device according to claim 1, wherein the substrate is a polymer.

4. A biosensing device according to claim 1, wherein the biosensing device is adapted for characterising target bioparticles with an average diameter of D, and wherein the binding cavities in the substrate have an average diameter in the range 1.5 times D to 0.5 times D.

5. A biosensing device according to claim 1, wherein the binding cavities in the substrate have an average diameter in the range 0.1 nm to 100 µm.

6. A biosensing device according to claim 1, wherein the structured substrate is a surface imprinted substrate or a molecularly imprinted substrate.

7. A biosensing device according to claim 1, wherein the surface of the binding cavities are functionalised for specific binding of the particles.

8. A biosensing device according to claim 1, wherein the processing means is adapted for determining a heat transfer resistivity as function of temperature.

9. A biosensing device according to claim 1, wherein the biosensing device comprises, at a side of the structured substrate opposite to the heating element, a fluid compartment for exposing that side of the structured substrate to a fluid, the second temperature sensor being positioned in the fluid compartment.

10. A biosensing device according to claim 1, wherein the processing means is adapted for outputting, based on the at least one heat transfer resistivity, a characteristic of the target bioparticles and/or wherein the heating element is controlled by a power resistor providing an input power, and/or wherein the first temperature sensor and/or the second temperature sensor is a thermocouple, and/or wherein the biosensing device comprises a controller for controlling the heating element and for controlling the temperature sensors for obtaining input power and temperature values for different temperatures as sensed with the first temperature sensor.

11. A method for characterising a target bioparticle, the target bioparticle not being a DNA bioparticle or an RNA bioparticle, the method comprising:
   providing a bio-sensing device according to claim 1;
   providing a heating power at a first side of the structured substrate using the heating element;
   sensing at least a temperature at the first side of the structured substrate using the first temperature sensor and at a second side, opposite to the first side with respect to the structured substrate using the second temperature sensor; and
   calculating at least one heat transfer resistivity value based on the temperature values obtained at the first side and the second side and the power using the processing means for deriving a characteristic of the target bioparticle from said heat transfer resistivity value.

12. A method according to claim 11, the method further comprising, prior to said providing a heating power and said sensing, rinsing the structured substrate with a fluid.

13. A method according to claim 11, wherein said calculating comprises determining a heat transfer resistivity as a function of temperature.

14. A method according to claim 11, wherein the method comprises providing a sample fluid in contact with the surface comprising the plurality of binding cavities and/or wherein said providing a bio-sensing device comprises binding the target bioparticles to the surface of the structured substrate comprising the plurality of binding cavities.

15. A controller for controlling a biosensing device according to claim 1, the controller being programmed for performing a method for characterising a target bioparticle, the target bioparticle not being a DNA bioparticle or an RNA bioparticle, the method comprising:
   obtaining a structured substrate having a surface comprising a plurality of binding cavities in which the target bioparticle can be bound;
   providing a heating power using a power at a first side of the structured substrate;

sensing at least a temperature at the first side of the structured substrate and at a second side, opposite to the first side with respect to the structured substrate; and calculating at least one heat transfer resistivity value based on the temperature values obtained at the first side and the second side and the power for deriving a characteristic of the target bioparticle from said heat transfer resistivity value.

* * * * *